US012241036B2

(12) United States Patent
Foody et al.

(10) Patent No.: US 12,241,036 B2
(45) Date of Patent: Mar. 4, 2025

(54) METHOD AND SYSTEM FOR PRODUCING A FUEL FROM BIOGAS

(71) Applicant: Iogen Corporation, Ottawa (CA)

(72) Inventors: Patrick J. Foody, Ottawa (CA); Brian Foody, Ottawa (CA); John Dechman, Ottawa (CA)

(73) Assignee: Iogen Corporation, Ottawa (CA)

( * ) Notice: Subject to any disclaimer, the term of this patent is extended or adjusted under 35 U.S.C. 154(b) by 939 days.

(21) Appl. No.: 17/142,537

(22) Filed: Jan. 6, 2021

(65) Prior Publication Data

US 2021/0155864 A1 May 27, 2021

Related U.S. Application Data

(63) Continuation-in-part of application No. PCT/CA2019/000103, filed on Jul. 9, 2019.

(Continued)

(51) Int. Cl.
*C10L 3/08* (2006.01)
*B01D 53/52* (2006.01)
(Continued)

(52) U.S. Cl.
CPC .............. *C10L 3/08* (2013.01); *B01D 53/526* (2013.01); *B01D 53/62* (2013.01); *C01B 3/34* (2013.01);
(Continued)

(58) Field of Classification Search
CPC .... C10L 3/08; C10L 3/104; C10L 1/02; C10L 1/04; C10L 2200/0469; C10L 2200/0492;
(Continued)

(56) References Cited

U.S. PATENT DOCUMENTS 4,380,242 A * 4/1983 Bresie .................... F17C 13/045
137/565.13
4,677,827 A * 7/1987 Shenoy ..................... F02C 1/02
60/648
(Continued)

FOREIGN PATENT DOCUMENTS

CA 2842759 A1 * 2/2013 ............... C01B 3/26
CA 2820733 7/2017
(Continued)

OTHER PUBLICATIONS

"Good Practices and Innovations in the Biogas Industry", European Biogas Association, Jan. 2018 (downloaded Aug. 28, 2019), in 100 pages. URL: http://european-biogas.eu/wp-content/uploads/2018/02/Success-Stories-EBA-2018.pdf.
(Continued)

*Primary Examiner* — Nicolas A Arnett
(74) *Attorney, Agent, or Firm* — Knobbe Martens Olson & Bear LLP

(57) ABSTRACT

A method for providing a fuel includes providing biogas from a plurality of biogas sources, the biogas from each biogas source produced in a process comprising filling a vessel with raw biogas or partially purified biogas to a pressure of at least 1500 psig and transporting the filled vessel to a centralized processing facility by vehicle. A fuel is produced in a fuel production process that includes feeding the biogas transported to the centralized processing facility to a biogas upgrading system that is configured to provide a carbon dioxide removed from the biogas. The removed carbon dioxide is provided for transport by vehicle and/or pipeline and/or sequestered to offset greenhouse gas emissions attributed to compressing the biogas for transport.

21 Claims, 10 Drawing Sheets

Related U.S. Application Data

(60) Provisional application No. 62/724,485, filed on Aug. 29, 2018, provisional application No. 62/696,006, filed on Jul. 10, 2018.

(51) Int. Cl.
    *B01D 53/62*     (2006.01)
    *C01B 3/34*     (2006.01)
    *C01B 3/48*     (2006.01)
    *C10L 1/02*     (2006.01)
    *C10L 1/04*     (2006.01)
    *C10L 3/10*     (2006.01)
    *C12P 5/02*     (2006.01)
    *F17C 5/00*     (2006.01)
    *F17C 7/00*     (2006.01)
    *F23D 14/28*     (2006.01)

(52) U.S. Cl.
    CPC .................. *C01B 3/48* (2013.01); *C10L 1/02* (2013.01); *C10L 1/04* (2013.01); *C10L 3/104* (2013.01); *C12P 5/023* (2013.01); *F17C 5/00* (2013.01); *F17C 7/00* (2013.01); *F23D 14/28* (2013.01); *B01D 2257/304* (2013.01); *B01D 2257/504* (2013.01); *B01D 2257/80* (2013.01); *B01D 2258/05* (2013.01); *C01B 2203/0238* (2013.01); *C01B 2203/0283* (2013.01); *C01B 2203/062* (2013.01); *C01B 2203/1241* (2013.01); *C01B 2203/1258* (2013.01); *C10L 2200/0469* (2013.01); *C10L 2200/0492* (2013.01); *C10L 2270/10* (2013.01); *C10L 2290/26* (2013.01); *C10L 2290/42* (2013.01); *C10L 2290/544* (2013.01); *F17C 2270/01* (2013.01)

(58) Field of Classification Search
    CPC ............ C10L 2270/10; C10L 2290/26; C10L 2290/42; C10L 2290/544; B01D 53/526; B01D 53/62; B01D 2257/304; B01D 2257/504; B01D 2257/80; B01D 2258/05; C01B 3/34; C01B 3/48; C01B 2203/0238; C01B 2203/0283; C01B 2203/062; C01B 2203/1241; C01B 2203/1258; F17C 5/00; F17C 7/00; F17C 2270/01; C12P 5/023; F23D 14/28
    See application file for complete search history.

(56) References Cited

U.S. PATENT DOCUMENTS

| | | | | |
|---|---|---|---|---|
| 5,570,729 | A * | 11/1996 | Mutter | F17C 13/02 141/2 |
| 5,603,360 | A * | 2/1997 | Teel | F17C 9/00 137/267 |
| 6,112,528 | A * | 9/2000 | Rigby | F17C 7/04 62/48.1 |
| 7,691,182 | B1 * | 4/2010 | Muradov | C10L 3/08 422/177 |
| 7,731,779 | B2 * | 6/2010 | Palumbo | C10L 3/102 95/52 |
| 8,007,567 | B2 * | 8/2011 | Roe | B01D 53/1475 95/193 |
| 8,373,305 | B2 * | 2/2013 | Adam | F02C 3/26 307/43 |
| 8,404,025 | B2 * | 3/2013 | Frisbie | H01M 8/0662 96/108 |
| 8,549,877 | B2 * | 10/2013 | Santos | F17D 1/05 62/619 |
| 8,658,026 | B2 * | 2/2014 | Foody | C10G 45/02 585/242 |
| 8,753,854 | B2 * | 6/2014 | Foody | G06Q 30/018 435/166 |
| 8,833,088 | B2 * | 9/2014 | Bayliff | F17C 7/00 62/5 |
| 8,945,373 | B2 * | 2/2015 | Foody | G06Q 30/018 208/143 |
| 8,999,036 | B2 * | 4/2015 | Pierce | B01D 53/002 95/47 |
| 9,040,271 | B2 * | 5/2015 | Foody | C10G 65/12 435/166 |
| 9,108,894 | B1 * | 8/2015 | Foody | C10L 1/023 |
| 9,145,300 | B1 * | 9/2015 | Foody | C01B 3/48 |
| 9,222,048 | B1 * | 12/2015 | Foody | C10L 3/06 |
| 9,234,627 | B2 * | 1/2016 | Cajiga | F17C 1/14 |
| 9,243,190 | B2 * | 1/2016 | Patience | C10G 2/334 |
| 9,506,605 | B2 * | 11/2016 | Paget | B01D 53/1475 |
| 9,514,464 | B2 * | 12/2016 | Foody | G06Q 30/018 |
| 9,535,045 | B2 * | 1/2017 | Gerhold | G01N 33/0011 |
| 9,605,286 | B2 * | 3/2017 | Foody | C12P 7/54 |
| 9,625,097 | B2 * | 4/2017 | Bayliff | F17C 7/00 |
| 9,625,099 | B2 * | 4/2017 | Ding | F17C 13/04 |
| 9,644,792 | B2 * | 5/2017 | Moszkowski | F17C 5/06 |
| 9,863,581 | B2 * | 1/2018 | Santos | F17C 5/06 |
| 9,969,949 | B1 * | 5/2018 | Foody | C12M 47/18 |
| 10,093,540 | B2 | 10/2018 | Foody | |
| 10,132,447 | B2 | 11/2018 | Whiteman et al. | |
| 10,183,267 | B2 | 1/2019 | Day et al. | |
| 10,202,622 | B2 | 2/2019 | Foody et al. | |
| 10,421,663 | B2 | 9/2019 | Foody | |
| 10,487,282 | B2 | 11/2019 | Foody et al. | |
| 10,619,173 | B2 | 4/2020 | Foody et al. | |
| 10,640,793 | B2 | 5/2020 | Foody et al. | |
| 10,723,621 | B2 | 7/2020 | Foody | |
| 10,760,024 | B2 * | 9/2020 | Foody | C10L 3/104 |
| 10,894,968 | B2 * | 1/2021 | Foody | C12P 7/54 |
| 10,968,151 | B1 * | 4/2021 | Whitmore | B01D 53/0462 |
| 10,981,784 | B2 * | 4/2021 | Foody | C10G 65/02 |
| 11,220,470 | B2 * | 1/2022 | Whitmore | B01D 53/864 |
| 11,299,686 | B2 * | 4/2022 | Foody | B01D 53/62 |
| 11,434,509 | B2 * | 9/2022 | Foody | C10L 1/04 |
| 11,708,313 | B2 * | 7/2023 | Whitmore | C10L 3/104 585/802 |
| 11,746,301 | B2 * | 9/2023 | Foody | C10L 3/104 518/702 |
| 11,760,630 | B2 * | 9/2023 | Foody | B01D 53/62 423/220 |
| 11,827,916 | B2 * | 11/2023 | Foody | C07C 29/1518 |
| 11,946,001 | B2 * | 4/2024 | Foody | C02F 11/04 |
| 11,946,006 | B2 * | 4/2024 | Foody | C12M 47/18 |
| 2003/0225169 | A1 | 12/2003 | Yetman | |
| 2006/0213370 | A1 | 9/2006 | Leonard et al. | |
| 2008/0134754 | A1 | 6/2008 | Funk | |
| 2008/0209916 | A1 | 9/2008 | White | |
| 2010/0000153 | A1 | 1/2010 | Kurkjian et al. | |
| 2010/0108567 | A1 * | 5/2010 | Medoff | C10G 3/00 208/113 |
| 2012/0308989 | A1 | 12/2012 | Barclay et al. | |
| 2013/0161235 | A1 | 6/2013 | Foody | |
| 2013/0183705 | A1 | 7/2013 | Barclay et al. | |
| 2013/0224808 | A1 | 8/2013 | Bell et al. | |
| 2014/0227751 | A1 * | 8/2014 | Datta | C12P 7/16 435/157 |
| 2014/0349360 | A1 * | 11/2014 | Zhang | C10L 1/02 435/162 |
| 2014/0370559 | A1 | 12/2014 | Oakley et al. | |
| 2015/0101671 | A1 | 4/2015 | Paget et al. | |
| 2015/0211684 | A1 * | 7/2015 | Santos | F17C 11/007 137/1 |
| 2015/0345708 | A1 | 12/2015 | Sloan et al. | |
| 2016/0245459 | A1 * | 8/2016 | Grimmer | F17C 5/06 |
| 2016/0247183 | A1 | 8/2016 | Foody | |
| 2016/0281927 | A1 * | 9/2016 | Bjørn | B63B 25/12 |
| 2016/0290563 | A1 * | 10/2016 | Diggins | F17C 7/00 |
| 2017/0074583 | A1 | 3/2017 | Tremblay | |
| 2017/0130901 | A1 | 5/2017 | Sloan et al. | |
| 2017/0241592 | A1 | 8/2017 | Whiteman et al. | |
| 2017/0304769 | A1 * | 10/2017 | Bigeard | B01D 53/265 |
| 2018/0079672 | A1 | 3/2018 | Meyer | |

(56) References Cited

U.S. PATENT DOCUMENTS

| | | | |
|---|---|---|---|
| 2018/0094772 | A1 | 4/2018 | Santos et al. |
| 2018/0112142 | A1 | 4/2018 | Foody et al. |
| 2018/0155649 | A1 | 6/2018 | Gerhold |
| 2018/0251372 | A1 | 9/2018 | Foody |
| 2019/0001263 | A1* | 1/2019 | Prince .................... F25J 3/0209 |
| 2019/0030482 | A1 | 1/2019 | Ding |
| 2019/0144890 | A1 | 5/2019 | Subbian et al. |
| 2019/0144895 | A1 | 5/2019 | Foody et al. |
| 2019/0185884 | A1 | 6/2019 | Foody |
| 2019/0224617 | A1* | 7/2019 | Mitariten ............... B01D 71/76 |
| 2019/0262770 | A1 | 8/2019 | Thygesen |
| 2020/0017787 | A1* | 1/2020 | Foody ............... B01D 53/1487 |
| 2020/0140901 | A1 | 5/2020 | Foody et al. |
| 2020/0148964 | A1* | 5/2020 | Foody ....................... C10L 1/02 |
| 2020/0318896 | A1* | 10/2020 | Prince .................... F25J 3/0233 |
| 2021/0055046 | A1* | 2/2021 | Prince .................... F25J 3/0233 |
| 2021/0060486 | A1* | 3/2021 | Prince .................... B01D 53/75 |
| 2021/0094894 | A1* | 4/2021 | Whitmore .............. G06Q 40/10 |
| 2021/0172677 | A1* | 6/2021 | Terrien .................. F25J 3/0209 |
| 2021/0275961 | A1* | 9/2021 | Foody ...................... C10L 3/08 |
| 2021/0317377 | A1* | 10/2021 | Foody ...................... C10L 1/04 |
| 2021/0324282 | A1* | 10/2021 | Foody .................. F17C 13/026 |
| 2022/0177792 | A1* | 6/2022 | Foody .................... C10L 3/104 |
| 2022/0267688 | A1* | 8/2022 | Foody .................... C12M 47/20 |
| 2023/0053930 | A1* | 2/2023 | Foody ..................... C02F 11/04 |
| 2023/0295523 | A1* | 9/2023 | Foody ....................... C12P 5/02 208/133 |
| 2024/0025739 | A1* | 1/2024 | Foody .................... C10K 1/005 |
| 2024/0123399 | A1 | 4/2024 | Buckenham |
| 2024/0209272 | A1* | 6/2024 | Foody .................... C12M 47/18 |

FOREIGN PATENT DOCUMENTS

| | | |
|---|---|---|
| DE | 10 2013 011 289 | 1/2015 |
| EP | 0 207 277 | 1/1990 |
| EP | 3 085 766 | 10/2016 |
| EP | 4 043 089 | 8/2022 |
| WO | WO 2010/006910 | 1/2010 |
| WO | WO 2011/101137 A1 | 8/2011 |
| WO | WO 2013/021140 | 2/2013 |
| WO | WO 2017/195103 | 11/2017 |
| WO | WO 2018/144328 | 8/2018 |
| WO | WO 2019/185315 | 10/2019 |
| WO | WO 2020/010430 | 1/2020 |
| WO | WO 2020/010431 | 1/2020 |
| WO | WO 2020/041857 | 3/2020 |
| WO | WO2021003564 | 1/2021 |
| WO | WO2021142528 | 7/2021 |
| WO | WO 2022/147610 | 7/2022 |

OTHER PUBLICATIONS

"IPCC Fourth Assessment Report: Climate Change 2007, 5.3.1.3 Alternative fuels—AR4 WGIII Chapter 5: Transport and its infrastructure", IPCC, accessed Oct. 14, 2020, in 5 pages. URL: https://archive.ipcc.ch/publications_and_data/ar4/wg3/en/ch5s5-3-1-3.html.

Beilstein et al., "Ethanol producers need to reduce their CI score—and quickly", Ethanol Producer Magazine, Oct. 31, 2019, in 5 pages. URL: http://ethanolproducer.com/articles/16668/ethanol-producers-need-to-reduce-their-ci-scoreundefinedand-quickly.

Biswas et al., "Biofuels and Their Production Through Different Catalytic Routes", Chemical and Biochemical Engineering Quarterly, Apr. 2017, vol. 31, pp. 47-62.

Hakawati et al., "What is the most energy efficient route for biogas utilization: Heat, electricity or transport?", Applied Energy, Nov. 2017, vol. 206, pp. 1076-1087.

Heijstra et al., "Gas Fermentation: Cellular Engineering Possibilities and Scale Up", Microbial Cell Factories, Apr. 2017, vol. 16, in 11 pages.

Hengeveld, E.J. et al., "Biogas infrastructures from farm to regional scale, prospects of biogas transport grids", Biomass and Bioenergy, Mar. 2016, vol. 86, pp. 43-52.

Hjort, A. et al., "Transport Alternatives for Biogas", BioMil AB, Nov. 2012, in 35 pages.

Hovland, J. et al., "Compression of raw biogas—A feasibility study", Tel-Tek, Apr. 2017, Report No. 2217020-1, in 12 pages.

Kapoor, R. et al., "Seventh Framework Programme Theme Energy", 7 Cooperation, downloaded on Aug. 27, 2019, in 59 pages. URL: http://www.valorgas.soton.ac.uk/Deliverables/120825_VALORGAS_241334_D5-2_rev[0].pdf.

Krich K. et al., "Chapter 4—Storage and Transportation of Biogas Biomethane", Biomethane from Dairy Waste: A Sourcebook for the Production and Use of Renewable Natural Gas in California, 2005 (downloaded on Aug. 23, 2019), in 10 pages. URL: http://www.suscon.org/pdfs/cowpower/biomethaneSourcebook/Chapter_4.pdf.

Munoth, K. et al., "Models for Decanting Gaseous Fuel Tanks: Simulations with GFSSP Thermal Model", Mechanical (and Materials) Engineering—Dissertations, University of Nebraska-Lincoln, Dec. 2016, in 133 pages.

Privat, R. et al., "Chapter 15—Predicting the Phase Equilibria of Carbon Dioxide Containing Mixtures Involved in CCS Processes Using the PPR78 Model," CO2 Sequestration and Valorization, Mar. 2014, in 20 pages.

Rufford et al., "The removal of CO2 and N2 from natural gas: A review of conventional and emerging process technologies", Journal of Petroleum Science and Engineering, vol. 94-95, Sep. 2012, pp. 123-154.

Schill, S., "California Carbon Check", Ethanol Producer Magazine, Jan. 23, 2019, in 3 pages. URL: http://www.ethanolproducer.com/articles/15888/california-carbon-check.

Stafford et al., "Biofuels Technology", United Nations University, WIDER Working Paper 2017/87, Apr. 2017, in 25 pages.

Torresani, M. et al., "Renewable Natural Gas Delivery Options. Getting your RNG to Market", Tetra Tech, Mar. 2018, Swanapalooza, Denver, Colorado, in 21 pages.

Unnasch, S., "GHG Emissions Reductions due to the RFS2: A 2018 Update", Life Cycle Associates, Feb. 6, 2019, in 19 pages.

Vitu, S. et al., "Predicting the phase equilibria of CO2 + hydrocarbon systems with the PPR78 model (PR EOS and kij calculated through a group contribution method)", Journal of Supercritical Fluids, May 2008, vol. 45, pp. 1-26.

Wang, Z., "Positioning your plant to maximize the opportunity created by low carbon fuel markets", ACE EcoEngineers, Aug. 16, 2018, in 27 pages.

International Search Report and Written Opinion mailed Oct. 18, 2019 for PCT Application No. PCT/CA2019/000104, filed Jul. 9, 2019.

International Search Report mailed Sep. 16, 2019 for PCT Application No. PCT/CA2019/000103, filed Jul. 9, 2019.

International Search Report mailed Nov. 8, 2019 for PCT Application No. PCT/CA2019/000122, filed Aug. 23, 2019.

Hengeveld et al., "When does decentralized production of biogas and centralized upgrading and injection into the natural gas grid make sense?", Biomass and Bioenergy, Jun. 2014, vol. 67, pp. 363-371.

Li et al., "Capturing CO2 from biogas plant", Energy Procedia, Jul. 2017, vol. 114, pp. 6030-6035.

Scholwin et al., "Biogas for Road Vehicles: Technology Brief", IRENA Mar. 2017 (Mar. 2017), in 62 pages.

International Preliminary Report on Patentability issued Jan. 21, 2021 for PCT Application No. PCT/CA2019/000104, filed Jul. 9, 2019.

International Search Report and Written Opinion mailed Sep. 16, 2019 for PCT Application No. PCT/CA2019/000103, filed Jul. 9, 2019.

International Preliminary Report on Patentability issued Jan. 21, 2021 for PCT Application No. PCT/CA2019/000103, filed Jul. 9, 2019.

International Search Report and Written Opinion mailed Mar. 17, 2022 for PCT Application No. PCT/CA2021/051845, filed Mar. 17, 2022.

International Search Report and Written Opinion mailed Nov. 8, 2019 for PCT Application No. PCT/CA2019/000122, filed Aug. 23, 2019.

(56) References Cited

OTHER PUBLICATIONS

International Preliminary Report on Patentability issued Mar. 11, 2021 for PCT Application No. PCT/CA2019/000122, filed Aug. 23, 2019.
Hovland, J., "Kompresjon av ra biogass", Tel-Tek, dated Jun. 1, 2017, in 24 pages.
International Preliminary Report on Patentability issued Jul. 4, 2023 for PCT Application No. PCT/CA2021/051845.
Invitation to Pay Additional Fees mailed Sep. 2, 2020 for PCT Application No. PCT/CA2020/050936, filed Jul. 6, 2020.
International Search Report and Written Opinion mailed Oct. 22, 2020 for PCT Application No. PCT/CA2020/050936, filed Jul. 6, 2020.
International Preliminary Report on Patentability issued Jan. 20, 2022 for PCT Application No. PCT/CA2020/050936, filed Jul. 6, 2020.
Office Action for U.S. Appl. No. 17/258,607, dated Jan. 5, 2024.
Restriction Requirement for U.S. Appl. No. 17/258,711 dated Dec. 29, 2023.
Office Action for U.S. Appl. No. 17/652,868, dated Mar. 6, 2023.
Notice of Allowance for U.S. Appl. No. 17/652,868, dated Apr. 19, 2023.
Chinese Office Action in CN Application No. 201980045125.7 dated May 27, 2022.
European Office Action in EP Application No. 19833590.3 dated Mar. 3, 2022.
European Office Action in EP Application No. 19833450.0 dated May 3, 2022.
European Office Action in EP Application No. 19853629.4 dated May 20, 2022.
Office Action for U.S. Appl. No. 17/258,607, dated Nov. 26, 2021.
Office Action for U.S. Appl. No. 17/258,607, dated May 12, 2022.
Hovland et al.; "Compression and transport of raw biogas", Sintef Tel-tek (2019).
IRENA (2018), Biogas for road vehicles: Technology brief, International Renewable Energy Agency, Abu Dhabi.
Advisory Action for U.S. Appl. No. 17/258,607, dated Jul. 22, 2022.
Advisory Action for U.S. Appl. No. 17/258,607, dated Sep. 1, 2022.
Office Action for U.S. Appl. No. 17/258,607, dated Oct. 27, 2022.
Office Action for U.S. Appl. No. 17/652,868, dated Oct. 6, 2022.
Chinese Office Action in CN Application No. 201980045125.7 dated Jan. 28, 2023.
Chinese Office Action in CN Application No. 201980045125.7 dated Apr. 28, 2023.
Office Action for U.S. Appl. No. 17/258,607, dated Mar. 17, 2022.
Office Action for U.S. Appl. No. 17/258,607, dated Apr. 13, 2023.
Canadian Office Action in CA Application No. 3,102,390 dated Mar. 1, 2024.
Canadian Office Action in CA Application No. 3,102,417 dated Feb. 2, 2024.
Canadian Office Action in CA Application No. 3,112,339 dated Mar. 20, 2024.
Canadian Office Action in CA Application No. 3,145,848 dated Mar. 1, 2024.
European Office Action in EP Application No. 20836871.2 dated Apr. 2, 2024.
Office Action for U.S. Appl. No. 17/258,607, dated Jun. 6, 2024.
Office Action for U.S. Appl. No. 17/258,711, dated Jun. 6, 2024.
Office Action for U.S. Appl. No. 17/271,014, dated Jul. 11, 2024.
Notice of Non-Compliant Appeal Brief for U.S. Appl. No. 17/258,607, dated Oct. 15, 2024.
Final Office Action for U.S. Appl. No. 17/258,711, dated Oct. 1, 2024.
European Office Action in EP Application No. 21916686.5 dated Oct. 24, 2024.
Office Action for U.S. Appl. No. 17/258,711, dated Dec. 13, 2024.
Canadian Office Action in CA Application No. 3,102,417 dated Nov. 22, 2024.

* cited by examiner

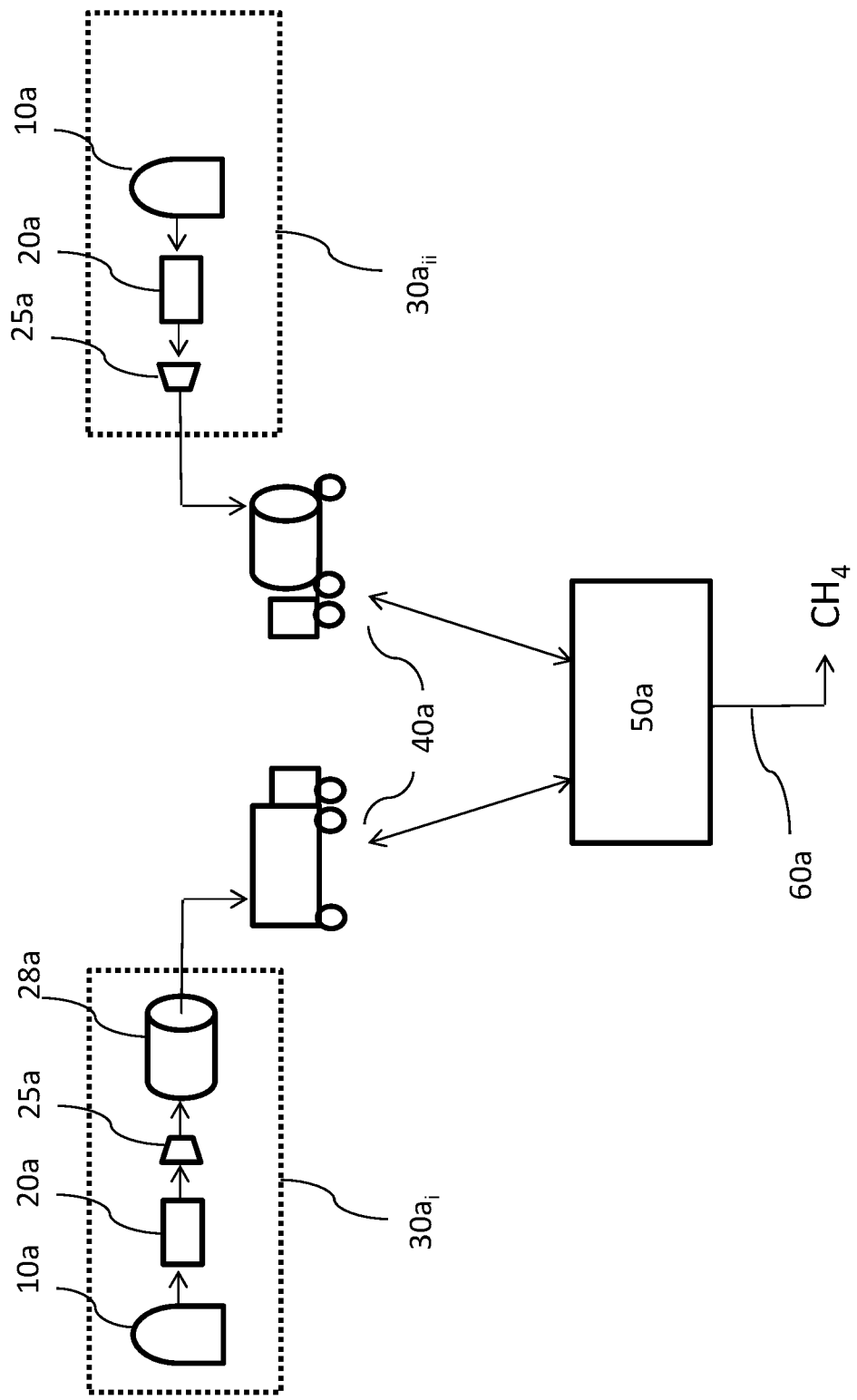

METHOD AND SYSTEM FOR PRODUCING A FUEL FROM BIOGAS

INCORPORATION BY REFERENCE TO ANY PRIORITY APPLICATIONS

This application is a continuation-in-part of PCT/CA2019/000103 filed Jul. 9, 2019, which claims benefit of U.S. Provisional Application No. 62/696,006 filed Jul. 10, 2018 and U.S. Provisional Application No. 62/724,485 filed Aug. 29, 2018, each of which is incorporated by reference herein in its entirety.

TECHNICAL FIELD

The present disclosure relates to a method and system for producing a fuel, and in particular, relates to a method and system for producing a fuel that includes transporting biogas from a plurality of biogas sources to a centralized processing facility by vehicle.

BACKGROUND

Biogas, which is a mixture of several gases, is typically produced by the breakdown of organic matter in low oxygen conditions. In particular, it is typically produced by the anaerobic digestion or fermentation of organic matter (e.g., manure, sewage sludge, municipal solid waste, biodegradable waste, biodegradable feedstock, etc.).

Biogas collected at its source (e.g., a landfill or anaerobic digester) may be referred to as raw biogas. The composition of raw biogas, which may vary with the type of organic matter from which it is derived, is predominately methane ($CH_4$) and carbon dioxide ($CO_2$), and may contain small and/or negligible amounts of nitrogen ($N_2$), hydrogen sulfide ($H_2S$), water ($H_2O$), ammonia ($NH_3$), hydrogen ($H_2$), carbon monoxide (CO), oxygen ($O_2$), volatile organic compounds (VOCs), and/or siloxanes. For example, without being limiting, the composition of raw biogas may include about 60% $CH_4$ (e.g., between about 35% and about 75%), about 35% $CO_2$ (e.g., between about 15% and about 65%), about 0-20% $N_2$, and about 0-5% $O_2$.

Biogas may be used without purification (i.e., raw biogas) or may be upgraded in a process that removes $CO_2$ and/or $N_2$ and typically some other contaminants, to increase the relative amount of $CH_4$, and thus the calorific value. When raw biogas is upgraded to the extent that it is substantially interchangeable with natural gas (e.g., meets or exceeds the specifications of a natural gas distribution system) it may be referred to as "renewable natural gas" or "RNG."

RNG may be used in place of natural gas in many applications, including the production of electricity, steam, or as a transportation fuel. RNG can be also used as a feedstock for chemical or fuel production. For example, RNG may be used as a feedstock to produce hydrogen, methanol, ethanol, gasoline, diesel, or dimethyl ether (DME).

While there are important environmental benefits to using biogas or RNG instead of natural gas, one barrier to using it in the production of fuels is that biogas is often produced on a small scale (e.g., relative to natural gas production). Fuel production from biogas typically requires biogas upgrading, and biogas upgrading and/or fuel production processes are typically associated with relatively high capital investment costs. Accordingly, fuel production from biogas is generally is not economically feasible for small scale productions (e.g., small farms, small landfills, or small wastewater treatment facilities). While there is interest in developing scalable and mobile technologies that can produce fuel from lower volumes of biogas, in practice, small scale biogas producers have been generally limited to using the biogas on-site and/or near the source of biogas. For example, small scale biogas producers may install a combined heat and power (CHP) unit, where the electricity generated may be used in the process and/or exported to the grid where feed-in-tariffs programs may exist.

SUMMARY

The present disclosure describes an improved method and/or system for producing a fuel wherein biogas is transported to a centralized processing facility where a fuel is produced using the biogas (e.g., RNG and/or ethanol). Since the centralized processing facility may receive biogas (e.g., raw or partially purified) from a plurality of biogas sources, the process may benefit from economies of scale (i.e., the cost of producing larger volumes is lower than the cost of processing smaller volumes, per unit volume). The disclosure also describes various embodiments where the greenhouse gas emissions attributed to compressing the biogas for transport and/or the transport of the biogas is offset by sequestering $CO_2$ removed from the biogas.

In accordance with one aspect of the instant invention there is provided a method for producing a fuel from biogas comprising: (a) providing biogas from a plurality of biogas sources, the biogas from each biogas source produced in a process comprising: (i) collecting raw biogas from one of the biogas sources in the plurality, the raw biogas comprising methane and carbon dioxide; (ii) optionally, subjecting the raw biogas to a partial purification to produce partially purified biogas, wherein the partial purification removes less than 75% of the carbon dioxide from the raw biogas; (iii) filling a vessel with the raw biogas or the partially purified biogas to a pressure of at least 1500 psig; (iv) transporting the filled vessel to a centralized processing facility by vehicle; and (v) removing the raw biogas or the partially purified biogas from the vessel transported to the centralized processing facility; (b) producing a fuel in a fuel production process, the fuel production processing comprising feeding the biogas provided in step (a) to a biogas upgrading system, the biogas upgrading system configured to provide a compressed stream of carbon dioxide removed from the biogas; and (c) providing carbon dioxide from the compressed stream of carbon dioxide for transport by vehicle, pipeline, or a combination thereof.

In accordance with one aspect of the instant invention there is provided a method for producing a fuel from biogas comprising: (a) providing biogas from a plurality of biogas sources, the biogas from each biogas source produced in a process comprising: (i) collecting raw biogas from one of the biogas sources in the plurality, the raw biogas comprising methane and carbon dioxide; (ii) optionally, subjecting the raw biogas to a partial purification to produce partially purified biogas, wherein the partial purification removes water and removes less than 75% of the carbon dioxide from the raw biogas; (iii) filling a vessel with the raw biogas or the partially purified biogas to a pressure of at least 1500 psig; (iv) transporting the filled vessel directly to a centralized processing facility by vehicle; and (v) removing the raw biogas or the partially purified biogas from the vessel transported to the centralized processing facility; (b) producing a fuel in a fuel production process, the fuel production processing comprising feeding the biogas provided in step (a) to a biogas upgrading system, the biogas upgrading system configured to remove carbon dioxide from the biogas; (c) processing the carbon dioxide removed in (b) for transport by vehicle, pipeline, or a combination thereof, the processing comprising cooling, compressing, or a combination thereof; and (d) sequestering the carbon dioxide processed in (c), thereby reducing a carbon intensity of the fuel produced in the fuel production process, the sequestering comprising sequestering an amount of carbon dioxide sufficient to substantially offset greenhouse gas emissions attributed to compressing and transporting the raw biogas or partially purified biogas.

In accordance with one aspect of the instant invention there is provided a method for producing a fuel from biogas comprising: (a) providing biogas from a plurality of biogas sources, the biogas from each biogas source produced in a process comprising: (i) collecting raw biogas from one of the biogas sources in the plurality, the raw biogas comprising methane and carbon dioxide; (ii) optionally, subjecting the raw biogas to a partial purification to produce partially purified biogas, wherein the partial purification removes water and removes less than 75% of the carbon dioxide from the raw biogas; (iii) filling a vessel with the raw biogas or the partially purified biogas to a pressure of at least 1500 psig; (iv) transporting the filled vessel to a centralized processing facility by vehicle; and (v) removing the raw biogas or the partially purified biogas from the vessel transported to the centralized processing facility; (b) producing a fuel in a fuel production process, the fuel production processing comprising feeding the biogas provided in step (a) to a biogas upgrading system, the biogas upgrading system configured to remove carbon dioxide from the biogas; (c) processing the carbon dioxide removed in (b) for transport by vehicle, pipeline, or a combination thereof, the processing comprising cooling, compressing, or a combination thereof; and (d) sequestering the carbon dioxide processed in (c), thereby reducing a carbon intensity of the fuel produced in the fuel production process, the sequestering comprising sequestering an amount of carbon dioxide sufficient to substantially offset greenhouse gas emissions attributed to compressing and transporting the raw biogas or partially purified biogas.

BRIEF DESCRIPTION OF THE DRAWINGS

FIG. 3a is a schematic diagram showing a system for providing a fuel in accordance with an embodiment;

DETAILED DESCRIPTION

Figure 1:
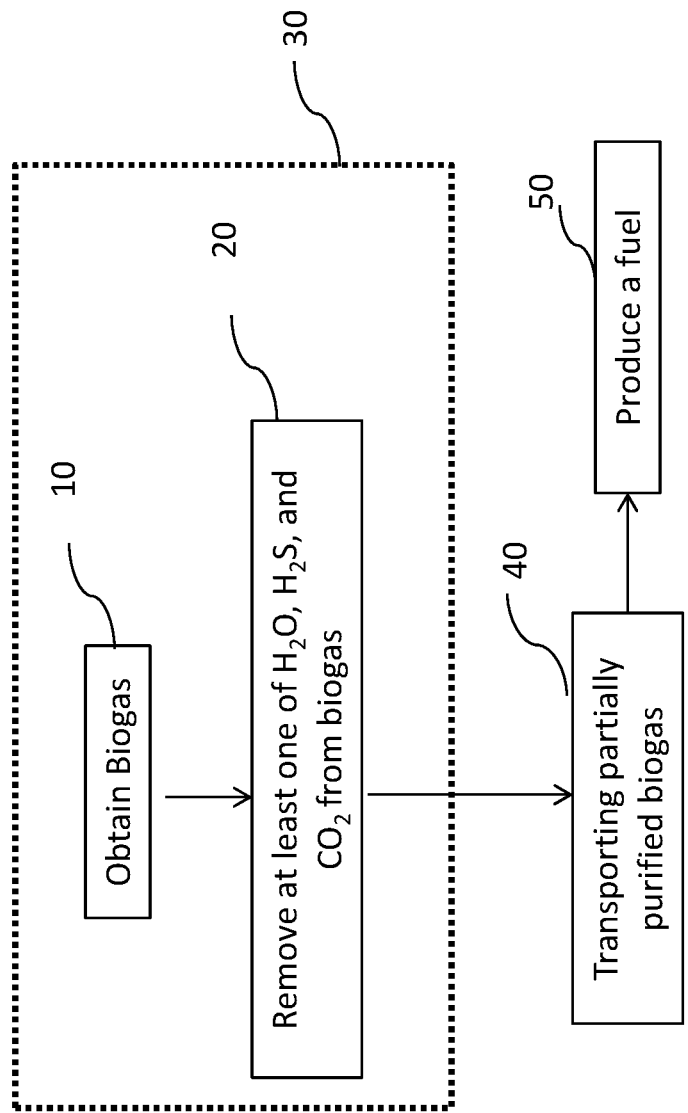
FIG. 1 is a flow diagram of a method according to one embodiment.

Certain exemplary embodiments of the invention now will be described in more detail, with reference to the drawings, in which like features are identified by like reference numerals. The invention may, however, be embodied in many different forms and should not be construed as limited to the embodiments set forth herein. The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, or the separating of components by the "removal" or "removing" of one component from another, those skilled in the art will understand that the order of addition/removal is not critical (unless stated otherwise). The terms "remove", "removing", and "removal", with reference to one or more impurities, contaminants, and/or constituents of biogas, includes partial removal. The terms "cause" or "causing", as used herein, may include arranging or bringing about a specific result (e.g., a withdrawal of a gas), either directly or indirectly, or to play a role in a series of activities through commercial arrangements such as a written agreement, verbal agreement, or contract. The term "associated with", as used herein with reference to two elements (e.g., a fuel credit associated with the transportation fuel), is intended to refer to the two elements being connected with each other, linked to each other, related in some way, dependent upon each other in some way, and/or in some relationship with each other. The terms "first", "second", etc., may be used to distinguish one element from another, and these elements should not be limited by these terms. The term "plurality", as used herein, refers to two or more. The term "providing" as used herein with respect to an element, refers to directly or indirectly obtaining the element and/or making the element available for use. Unless defined otherwise, all technical and scientific terms used herein have the same meanings as commonly understood by one of ordinary skill in the art.

Referring to FIG. 1, there is shown a method in accordance with one embodiment. In 10, raw biogas is obtained (e.g., withdrawn from the source). In 20, the raw biogas, which contains both $CH_4$ and $CO_2$, is subject to a partial purification process (e.g., that removes at least one of $H_2O$, $H_2S$, and $CO_2$) to produce partially purified biogas. In 40, the resulting partially purified biogas is collected and/or transported (e.g., by truck, rail, or ship). In 50, the partially purified biogas is used to produce the fuel (e.g., a transportation fuel). In some embodiments, the partial purification 20 is optional and raw biogas is transported.

Figure 2:
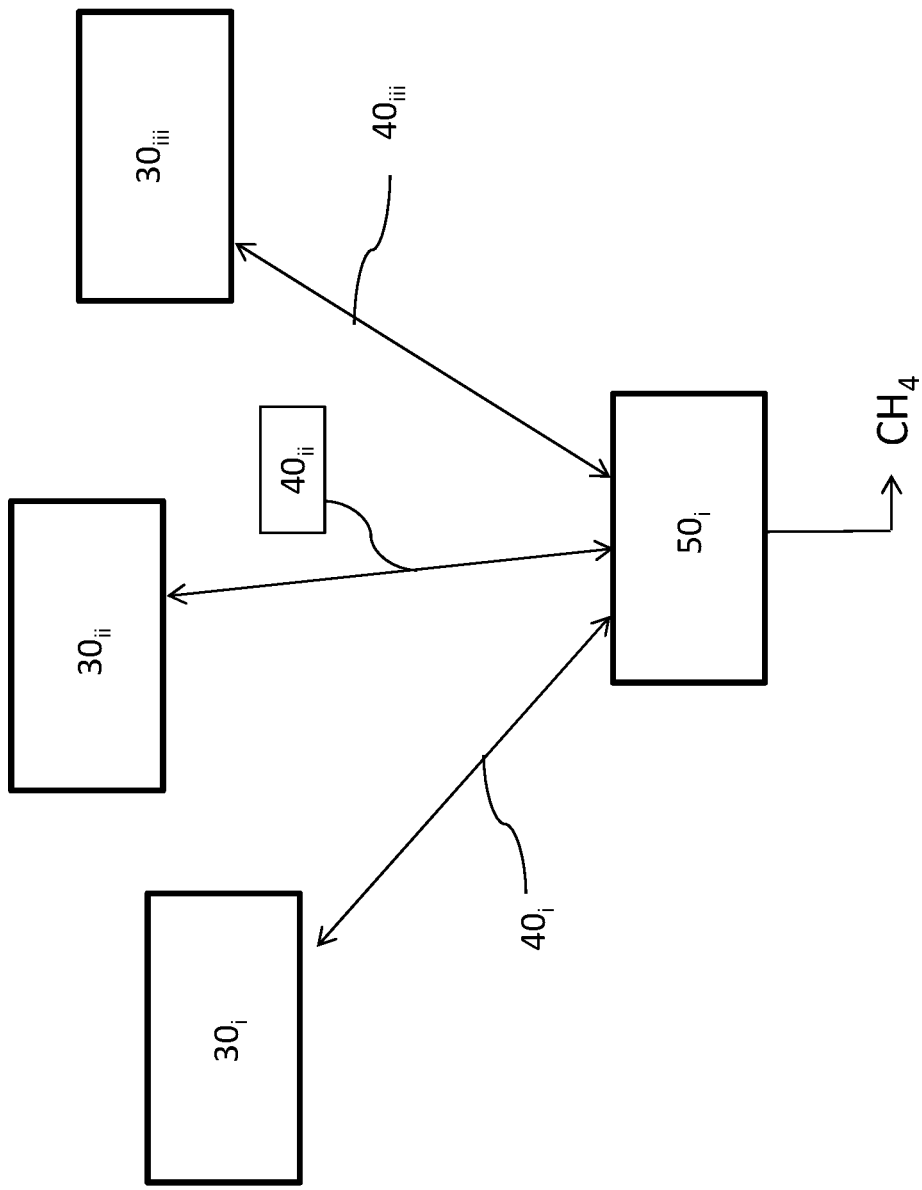
FIG. 2 is a flow diagram of a method according to one embodiment.

Referring to FIG. 2, the steps of obtaining raw biogas 10 and partially purifying the raw biogas 20, collectively represented as 30, are performed at a plurality of pre-processing sites $30_i$, $30_{ii}$, $30_{iii}$. The raw or partially purified biogas obtained at each pre-processing site is collected and/or transported via a collection system (e.g., $40_i$, $40_{ii}$, and/or $40_{iii}$) to the centralized processing facility $50_i$. Advantageously, this hub-and-spoke configuration improves efficiency. In FIG. 2, the centralized processing facility is illustrated as producing RNG, however, in some embodiments, the centralized processing facility alternatively or additionally produces another fuel using the biogas.

Biogas Production

For purposes herein, the term "biogas", which refers to a gas mixture that contains methane produced from the anaerobic digestion of organic matter, encompasses raw biogas and partially purified biogas, but does not encompass RNG, unless specified otherwise. Raw biogas refers to biogas before it is treated to remove any chemical components (e.g., $CO_2$, $H_2S$, $H_2O$, $N_2$, $NH_3$, $H_2$, CO, $O_2$, VOCs, and/or siloxanes). Partially purified biogas refers to biogas that has been treated to remove non-methane components (e.g., $CO_2$, $H_2S$, $H_2O$, $N_2$, $NH_3$, $H_2$, CO, $O_2$, VOCs, and/or siloxanes), and requires further purification in order to meet pipeline specifications (e.g., it may contain one or more non-methane components in an amount that causes it to fall short of meeting natural gas pipeline standards or specifications).

In general, the raw biogas obtained in 10 and/or at each pre-processing site $30_i$, $30_{ii}$, $30_{iii}$ can be obtained from any source that produces biogas (e.g., a landfill or anaerobic digester). For example, the biogas may be obtained from a landfill and/or from a biogas source that includes one or more anaerobic digesters. In embodiments where the biogas is obtained from a biogas source that includes one or more anaerobic digesters, the digesters may be connected in series and/or in parallel, may be single-stage or multi-stage digestion systems, and/or may be designed and/or operated in a number of configurations including batch or continuous, mesophilic or thermophilic temperature ranges, and low, medium, or high rates. In addition, in embodiments where the biogas is obtained from a biogas source that includes one or more anaerobic digesters, the digesters may be used for manure or other farm waste, for wastewater treatment, for treating industrial waste, and/or for treating wastewater, wastes, and/or residues from an ethanol process. In one embodiment, the biogas is sourced from one or more anaerobic digesters at a dairy farm. In one embodiment, the biogas is sourced from one or more anaerobic digesters at a swine farm. In one embodiment, the biogas is sourced from a landfill site. In one embodiment, the biogas is sourced from a wastewater treatment plant (WWTP).

Raw biogas may, for example, have a methane ($CH_4$) content between about 35% and 75% (e.g., average of about 60%) and a carbon dioxide ($CO_2$) content between about 15% and 65% (e.g., average of about 35%), depending on the source. For example, without being limiting, biogas sources based on anaerobic digesters fed agricultural waste may have a methane content between about 50% and 75%, whereas biogas from a landfill site may have a methane content between about 25% and 65%. In one embodiment, the raw biogas has a methane content between about 25% and 75% and a carbon dioxide content between about 15% and 65%, and the carbon dioxide and methane make up at least 75% of the biogas by volume.

In one embodiment, the biogas source (e.g., based on landfill or anaerobic digester) produces raw biogas at a rate less than 6000 SCFM (standard cubic feet per minute). In one embodiment, the biogas source produces raw biogas at a rate less than 5000 SCFM. In one embodiment, the biogas source produces raw biogas at a rate between 100 and 3000 SCFM. In one embodiment, the biogas source produces raw biogas at a rate between 1000 and 3000 SCFM. In one embodiment, the biogas source produces raw biogas at a rate between 1500 and 3000 SCFM.

The percentages used to quantify gas composition and/or a specific gas content, as used herein, are expressed as mol %, unless otherwise specified.

Partial Purification

In general, the partial purification in 20 and/or at each pre-processing site $30_i$, $30_{ii}$, $30_{iii}$ will remove $H_2O$, $H_2S$, and/or $CO_2$ from the raw biogas to provide partially purified biogas having a $H_2O$ content, $H_2S$ content, and/or $CO_2$ content that is less than that of the raw biogas. Optionally, one or more other non-methane components are removed.

In general, the partial purification provided in 20 and/or at each pre-processing site $30_i$, $30_{ii}$, $30_{iii}$ does not produce a gas that meets applicable quality specifications for injection into the natural gas distribution system (e.g., pipeline standards) and/or is suitable for use in the transportation sector, but rather, requires further purification in order to qualify as RNG under applicable regulations. For example, in one embodiment, the partially purified biogas has a non-methane content of at least 20%. In one embodiment, the partially purified biogas has a non-methane content of at least 15%. In one embodiment, the partially purified biogas has a non-methane content of at least 10%. In one embodiment, the partially purified biogas has a non-methane content of at least 8%. In one embodiment, the partially purified biogas has a non-methane content of at least 6%. In one embodiment, the partially purified biogas has an inert content (e.g., $CO_2$, $N_2$, helium, argon, neon) that is greater than 10%.

In one embodiment, the partially purified biogas has a $CO_2$ content less than 10%, less than 9%, less than 8%, less than 7%, less than 6%, or less than 5%. In one embodiment, the partially purified biogas has a $CO_2$ content between about 4% and 8%, between about 4% and 9%, or between about 4% and 10%. In one embodiment, the partially purified biogas has a $CH_4$ content between about 50% and about 93%. In one embodiment, the partially purified biogas has a $CH_4$ content between about 50% and about 90% and an $N_2$ content between about 10% and 20%. In one embodiment, the partially purified biogas has a $CH_4$ content between about 80% and about 90% and an $N_2$ content between about 10% and 20%. In one embodiment, the partially purified biogas has a $CH_4$ content between about 72% and about 90%, a $CO_2$ content between about 0 and 8%, and an $N_2$ content between about 5% and 20%. In one embodiment, the partially purified biogas has a combined $CH_4$ and $N_2$ content that is greater than 98%, where the $N_2$ content is at least 5%. In one embodiment, the partially purified biogas has a combined $CH_4$ and $N_2$ content that is greater than 98%, and a $CO_2$ content that is less than 1%. In one embodiment, the partially purified biogas has a combined $CH_4$ and $N_2$ content that is greater than 98%, where the $N_2$ content is at least 5%, and wherein the $CO_2$ content is less than 200, 100, 50, or 30 ppm.

In one embodiment, the partial purification of the raw biogas is provided near the source of raw biogas (e.g., at a pre-processing site). For example, in one embodiment a pre-processing site is fed raw biogas directly from a biogas source and/or is located at a biogas plant or landfill. In one embodiment, the pre-processing site is fed raw biogas from a biogas pipeline fed from one or more biogas sources. The term "pipeline", as used herein, refers to a single pipe or an interconnected network of pipes (e.g., physically connected), including any associated pumps and valves.

In one embodiment, the partial purification of the raw biogas is provided using a stationary purification system (e.g., installed at the pre-processing site). Using a stationary purification system advantageously allows the partial purification system to be readily available on-site to at least partially purify the raw biogas as it is produced. Moreover, since the purification system is stationary it can be designed and/or selected in dependence upon the average composition of the raw biogas from that particular source. Furthermore, since the purification system remains on-site (e.g., is not transported with the vessels) more partially purified biogas may be transported. For purposes herein, the term "stationary" as used with reference to a purification system, refers to the purification system not moving from the pre-processing site or facility at which it is used (although it may move within the pre-processing site or facility).

In one embodiment, at least part of the partial purification is achieved using a stationary purification system based on any suitable method/technology, or combination of methods/technologies, in one or more stages, as known in the art. For example. $H_2O$ may be removed using a standard biogas dehumidifier, whereas $H_2S$ may be removed using a commercial $H_2S$ removal unit (e.g., based on activated carbon, molecular sieve, iron sponge, water scrubbing, NaOH washing, and/or biofilter or biotrickling filter technologies). Some $H_2S$ may also be removed during the water removal step, if present. $O_2$ may be removed by catalytic oxidation, membranes, or low pressure PSA. $CO_2$ may be removed by absorption (e.g., water scrubbing, organic physical scrubbing, chemical scrubbing), pressure swing adsorption (PSA), membrane permeation, and/or cryogenic upgrading. In one embodiment, the partial purification system includes a dehumidifier, a scrubber, a membrane unit, a solvent extraction unit, a pressure swing adsorption unit, and/or a cryogenic unit.

In one embodiment, the partial purification is essentially a cleaning or pre-cleaning stage that does not significantly remove $CO_2$ or $N_2$. For example, in one embodiment, the partial purification removes $H_2O$ and/or $H_2S$, but does not significantly remove $CO_2$ or $N_2$.

In one embodiment, the partial purification removes $H_2O$. Raw biogas may be fully saturated with water vapour and/or may have a water content of about 7% (at 40° C.). Removing $H_2O$ is advantageous since moisture can condense into water or ice when passing from high to low pressure systems, which may cause corrosion, may result in clogging, and/or may interfere with gas flow and pressure measurements (e.g., causing system control problems). In addition, the presence of water may cause hydrates to form. In one embodiment, the partial purification removes more than 90%, 92%, 94%, 96%, or 98% of the $H_2O$ present in the raw biogas. In one embodiment, the partial purification removes more than 99% of the $H_2O$ present in the raw biogas. In one embodiment, the partial purification removes sufficient $H_2O$ from the raw biogas that the $H_2O$ content of partially purified biogas more than meets the $H_2O$ content specifications for RNG. In one embodiment, the partial purification 20 does not remove $H_2O$. In one embodiment, the partial purification 20 removes sufficient moisture to provide the partially purified biogas with an $H_2O$ concentration of less than 0.4 $g/m^3$ of biogas. In one embodiment, the partial purification 20 removes sufficient moisture to provide the partially purified biogas with an $H_2O$ concentration of less than 0.2 $g/m^3$ of biogas. In one embodiment, the partial purification includes an $H_2O$ removal stage that uses refrigeration techniques or desiccant drying. In one embodiment, the partial purification includes multi-stages of $H_2O$ removal (e.g., first stage of $H_2O$ removal followed by a second stage of $H_2O$ removal), which may or may not be consecutive.

In one embodiment, the partial purification removes $H_2S$. Raw biogas may have an $H_2S$ concentration between about 0 and about 6700 ppm(v) (e.g., 0-10,000 $mg/m^3$). For example, without being limiting, biogas derived from agricultural waste may have an $H_2S$ concentration between 0-4000 ppm(v), whereas biogas from a landfill may have an $H_2S$ concentration between 0 and 1000 ppm(v). $H_2S$ is both poisonous and corrosive, and can damage piping, equipment, and instrumentation. $H_2S$ can be reactive with many metals, and the reactivity can be higher at higher concentration and pressure, and/or in the presence of water. In one embodiment, the partial purification removes more than 90%, 92%, 94%, 96%, or 98% of the $H_2S$ present in the raw biogas. In one embodiment, the partial purification removes more than 99% of the $H_2S$ present in the raw biogas. In one embodiment, the partial purification removes sufficient $H_2S$ from the raw biogas that the $H_2S$ content of partially purified biogas more than meets the $H_2S$ content specifications for RNG. In one embodiment, the partial purification removes sufficient $H_2S$ from the raw biogas that the $H_2S$ content of partially purified biogas is safer to transport but requires additional $H_2S$ removal to meet RNG standards. In one embodiment, the partial purification 20 does not remove $H_2S$. In one embodiment, the partial purification removes sufficient $H_2S$ from the raw biogas that the $H_2S$ concentration of partially purified biogas is less than 200 ppm(v). In one embodiment, the partial purification removes sufficient $H_2S$ from the raw biogas that the $H_2S$ concentration of partially purified biogas is less than 100 ppm(v). In one embodiment, the partial purification removes sufficient $H_2S$ from the raw biogas that the $H_2S$ concentration of partially purified biogas is between 20 ppm(v) and 50 ppm(v). In one embodiment, the partial purification removes sufficient $H_2S$ from the raw biogas that the $H_2S$ concentration of partially purified biogas is less than 50, 40, 30, 20, or 10 ppm(v). In one embodiment, the partial purification removes sufficient $H_2S$ from the raw biogas that the $H_2S$ concentration of partially purified biogas is less than about 6 ppm(v). In one embodiment, the partial purification includes a first stage of $H_2S$ removal (e.g., biological) followed by second stage of $H_2S$ removal (e.g., an adsorption bed), which may or may not be consecutive.

In one embodiment, the partial purification removes $H_2O$ and $H_2S$. Contaminants such as $O_2$, $NH_3$, VOCs, siloxanes, and/or particulates are optionally removed, although this is not necessary. Although the biogas upgrading system used in 50 may include $H_2O$ and/or $H_2S$ removal, it can be advantageous to remove $H_2O$ and/or $H_2S$ prior to collection and/or transport. For example, transporting gas with $H_2S$ creates the risk that in the event of a leak or accident, $H_2S$ leaks out, thereby creating toxic gas and safety issues. This risk is eliminated or reduced when the partial purification includes $H_2S$ removal. In addition, since $H_2S$, and in particular the combination of $H_2O$ and $H_2S$, can cause corrosion problems, removing the $H_2O$ and/or $H_2S$ can reduce equipment maintenance costs, and provide flexibility on construction materials for mobile storage tanks. Furthermore, removing $H_2S$ may improve the $CO_2/CH_4$ separation if present during the partial purification.

In one embodiment, the partial purification 20 removes $O_2$. Removing $O_2$ maybe particularly advantageous prior to compression and transport.

In one embodiment, the partial purification 20 removes $CO_2$. In one embodiment, the partial purification removes $CO_2$ and/or $N_2$. Contaminants such as $H_2O$, $H_2S$, $O_2$, $NH_3$, VOCs, siloxanes, and/or particulates are optionally removed. For example, some $CO_2$ removal technologies also remove $H_2S$. Although the biogas upgrading system used in 50 will typically include $CO_2$ and/or $N_2$ removal, it can be advantageous to remove $CO_2$ prior to collecting and/or transporting the partially purified biogas. Even removing half of the $CO_2$ present in biogas can significantly reduce the amount of gas that needs to be compressed and/or transported.

With specific regard to the advantages of $CO_2$ removal, consider the following. For every quantity of biogas compressed and transported, a certain amount of equipment and energy is required. This equipment and/or energy is associated with additional cost and greenhouse gas (GHG) emissions. Since raw biogas can contain about 60% $CO_2$, removing $CO_2$ from raw biogas can significantly reduce the amount of gas processed, and thus reduce the compression and/or transportation cost per unit of energy delivered (i.e., which is related to the amount of methane). For example, removing a significant quantity of $CO_2$ can decrease the number of trucks and/or runs required. Accordingly, transporting partially purified biogas, particularly when $CO_2$ has been removed, is generally more efficient (e.g., in terms of both costs and GHG emission reductions) than transporting raw biogas.

In addition, the $CO_2$ in raw biogas can make it more challenging (e.g., there can be phase change issues when $CO_2$ is compressed or depressurized) and/or less energy efficient to compress relative to pure $CH_4$. Accordingly, removing even a portion of the $CO_2$ from raw biogas can improve compression and/or transport to the centralized processing facility, by simplifying compressing and reducing compressions costs (e.g., relative to compressing raw biogas).

In one embodiment, the partial purification removes more than 90%, 92%, 94%, 96%, or 98% of the $CO_2$ present in the raw biogas. In one embodiment, the partial purification removes more than 20%, 30%, 40% or 50% of the $CO_2$ present in the raw biogas. In one embodiment, the partial purification removes between about 5% and 20% of the $CO_2$ present in the raw biogas. In one embodiment, the partial purification removes less than 5% of the $CO_2$ present in the raw biogas. In one embodiment, the partial purification does not substantially remove $CO_2$. In one embodiment, no more than 75% of the $CO_2$ is removed.

In one embodiment, the partial purification removes sufficient $CO_2$ to increase the heating value of the biogas by at least 50 BTU/scf, at least 100 BTU/scf, at least 150 BTU/scf, at least 200 BTU/scf, or at least 250 BTU/scf. For example, in one embodiment, the partial purification increases the heating value of the biogas (e.g., which may be about 350-500 BTU/scf) to at least 600 BTU/scf, at least 700 BTU/scf, or at least 800 BTU/scf, but retains sufficient $CO_2$ and/or $N_2$ such that the heating value does not exceed 900 BTU/scf, 925 BTU/scf, or 950 BTU/scf. The term "heating value", as used herein, refers to the higher heating value (HHV), unless otherwise specified.

In one embodiment, the partial purification removes sufficient $CO_2$ from the raw biogas that the $CO_2$ content of partially purified biogas is less than 25%. In one embodiment, the partial purification removes sufficient $CO_2$ from the raw biogas that the $CO_2$ content of partially purified biogas is less than 20%, 15%, 10%, or 8%. In one embodiment, the partial purification removes sufficient $CO_2$ from the raw biogas that the $CO_2$ content of partially purified biogas is less than 5%. In one embodiment, the partial purification removes sufficient $CO_2$ from the raw biogas that the $CO_2$ content of partially purified biogas is less than 4%.

In one embodiment, between 10% and 85% of the $CO_2$ is removed. In one between 20% and 80% of the $CO_2$ is removed. In one embodiment between 40% and 60% of the $CO_2$ is removed. In one embodiment between 84% and 90% of the $CO_2$ is removed. In one embodiment, the partial purification system used removes more than 10% and less than 95% of the $CO_2$ in the biogas. For example, removing 10% of the $CO_2$ from a biogas containing 50% $CH_4$, 38% $CO_2$, 10% $N_2$, and 2% $O_2$, provides a partially purified biogas containing 52% $CH_4$, 35.6% $CO_2$, 10.4% $N_2$, and 2.1% $O_2$, whereas removing 85% of the $CO_2$ from the biogas containing 50% $CH_4$, 38% $CO_2$, 10% $N_2$, and 2% $O_2$, provides a partially purified biogas containing 73.9% $CH_4$, 8.4% $CO_2$, 14.8% $N_2$, and 3% $O_2$. Removing only enough $CO_2$ to yield a partially purified biogas having a $CH_4$ content that is less than 85% is advantageous in that such upgrading is relatively easy and/or can be achieved using commercial systems that are less costly. In one embodiment, sufficient $CO_2$ is removed so as to provide the partially purified biogas with a $CH_4$ content that is at least 70% and no more than 90%, which may provide a good balance between upgrading cost and compressibility.

In this embodiment, the relative high pressures required for transport are used to improve the partial purification. In one embodiment, the partial purification includes a water based removal of $CO_2$.

Although it can be advantageous to remove $CO_2$, $H_2O$, and/or $H_2S$ from raw biogas prior to collection and/or transport, doing so has the potential to increase capital investment and/or operating costs (e.g., for the biogas producer or another party), while potentially introducing a redundant step. Nevertheless, this approach offers some unique benefits.

One advantage is that since the partial purification can yield a partially purified biogas having a non-methane content that is greater than 10%, while still being effective for its purpose, a relatively simple and/or inexpensive partial purification module or system can be used. Such systems may have a relatively low capital investment, operating costs, associated maintenance, space requirements, and/or appear more user-friendly. For example, a water scrubber system or a relatively simple membrane system (e.g., single stage and/or low permselectivity for $CO_2/CH_4$ separations) are relatively affordable for small scale use, and are particularly suitable for partial purification of raw biogas prior to transport to a centralized processing facility.

Accordingly, when the centralized processing facility includes one or more purification units, the purification of the biogas may be conducted in two stages. The first stage, which provides a crude purification, is provided using relatively simple and/or inexpensive equipment. The second stage, which provides a more rigorous purification and is more challenging technically, can be conducted at the centralized processing facility. In this case, the more difficult second stage of purification still benefits from the economies of scale.

In addition, although providing partial purification prior to collection and transport increases capital investment costs (by forsaking the economies of scale of centralized processing for a portion of the purification, with multiple smaller partial purification systems instead of a centralized facility), the aggregate cost of transporting can be reduced by permitting lower cost materials of construction or by reducing the bulk quantity that needs to be transported.

Another advantage is since the partial purification can focus on removing fewer components (e.g., $H_2O$, $H_2S$, and/or $CO_2$), these components may be removed using a stationary system that can remove them more efficiently and/or cost effectively than a mobile biogas upgrading or purification system. For example, removing $H_2S$ at the pre-processing site with a dedicated $H_2S$ removal system can be advantageously efficient. Moreover, it facilitates transport of the biogas at $H_2S$ levels that meet transportation standards.

Another advantage is that with some types of biogas upgrading technologies, such as simple membrane systems, there typically is a trade-off between the recovery of a component and its purity. For example, when using a simple membrane system to separate $CH_4$ and $CO_2$, high $CH_4$ yields are typically associated with a relatively large $CO_2$ content. Alternatively, if relatively pure $CH_4$ is to be recovered (e.g., with little $CO_2$), the $CH_4$ yield will be lower since some of the $CH_4$ will be lost in the off-gas with the $CO_2$. In conventional biogas upgrading, the goal is to obtain relatively pure $CH_4$, and thus a significant amount of the $CH_4$ can be lost as methane "slip". However, when providing partial purification prior to transport to a centralized processing facility, the goal can be to maximize the amount of $CH_4$ transported to the centralized processing facility, while removing only some of the $CO_2$. Accordingly, in this configuration, the trade-off is an advantage and/or facilitates the use of less expensive equipment.

Yet another advantage is that providing partial purification at or near the source of raw biogas (e.g., a biogas plant) can provide additional value-added products and/or facilitate recycling of the removed components. For example, if water is removed, it can be recycled. In embodiments where the partial purification includes removing $CO_2$, the removed $CO_2$ can be recycled(e.g., injected into an anaerobic digester, fed to a greenhouse, etc.) or can be provided as a value added product.

Notably, in types of biogas upgrading technologies where there is a trade-off between the recovery of a component and its purity, such as simple membrane systems, when the purity of the product (e.g., $CH_4$) is low, the purity of the removed product (e.g., $CO_2$) is often high. Accordingly, the off-gas of the partial purification system may be sufficiently clean for direct discharge to the atmosphere (e.g., the $CO_2$ removed from the raw biogas is biogenic). Another advantage is that, with some types of biogas upgrading technologies, such as membrane systems, some methane may be lost in an off-gas (e.g., methane slip). In this case, the methane in the off-gas can be combusted to provide energy for the compression.

In one embodiment, the partially purified biogas is stored prior to collection and transport (e.g., at the pre-processing site). The partially purified biogas can be stored using any suitable storage system (e.g., including any vessel). For example, the partially purified biogas can be stored in a storage system that includes permanent storage tanks and/or mobile storage tanks.

In one embodiment, the partially purified biogas is stored in one or more mobile storage tanks (e.g., a batch container that can contain gas and that can be moved from one location to another). For example, in one embodiment, the partially purified biogas is fed into one or more cylinders mounted to or within a trailer, skid, or shipping container that is attachable and detachable from a truck (e.g., a tractor unit). Some examples of systems that include one or more mobile storage tanks are tube trailers and cylinder trailers.

In one embodiment, the partially purified biogas is fed in one or more mobile storage tanks as it is produced (e.g., as the partially purified biogas is produced, it is fed to the one or more mobile storage tanks where it accumulates). The one or more mobile storage tanks may be arranged to fill in tandem or parallel. For example, in one embodiment, partially purified biogas is fed to a single trailer until the trailer is at capacity before the partially purified biogas is fed to another trailer. In one embodiment, partially purified biogas is simultaneously fed to a plurality of trailers. Feeding the partially purified biogas to a plurality of trailers is advantageous in that the fill rate may be lower. A lower fill rate may allow more time for the heat generated from the compression to dissipate and/or may increase the duration between collection times.

In one embodiment, the partially purified biogas is compressed before being fed into one or more mobile storage tanks (e.g., each mobile storage tank may include one or more pressure vessels). In this embodiment, the pre-processing site may include one or more compressors (e.g., where each compressor may be a multistage compressor). In one embodiment, the pre-processing site includes a standard CNG compressor. In one embodiment, the pre-processing site includes a 3-stage non-lubricated compressor configured to compress partially purified biogas prior to being fed to the one or more mobile storage tanks.

In many instances, the raw biogas obtained in 10 will be obtained at pressures less than 10 psi (e.g., 2-3 psi). Depending on the system and/or technology used for the partial purification, the pressure of the partially purified biogas produced in 20 may be at a higher pressure (e.g., about 200 psig for a membrane separation). It can be particularly advantageous to compress the partially purified biogas to pressures above 1500 psig for storage in a mobile storage tank, as many trailers are designed to transport high-pressure gas (e.g., about 2000-3600 psig), and thus this increases the amount of methane per tank. In one embodiment, the partially purified biogas is compressed to at least 1000 psig. In one embodiment, the partially purified biogas is compressed to at least 1500 psig. In one embodiment, the partially purified biogas is compressed to at least 2000 psig. In one embodiment, the partially purified biogas is compressed to between 2000 psig and 4500 psig. In one embodiment, the partially purified biogas is compressed to between 2400 psig and 4000 psig. In one embodiment, the partially purified biogas is compressed to between 2800 psi and 4200 psig. In one embodiment, the partially purified biogas is compressed to between 3400 psig and 3600 psig. In one embodiment, the partially purified biogas is compressed to about 3500 psig. In one embodiment, the partially purified biogas is compressed to about 3000 psig.

Filling one or more mobile storage tanks with compressed partially purified biogas as the partially purified biogas is produced is advantageous in that it may obviate the need for buffer storage, may obviate transferring the biogas gas between storage tanks (e.g., which may involve compression and/or decompression), and will generally be more efficient in terms of collecting the partially purified biogas for transport back to the centralized processing facility. For example, once a mobile storage tank is at the desired fill level (e.g., at capacity), the entire tank can be collected (e.g., picked-up) and/or transported to the centralized processing facility. For example, if the mobile storage tank is part of a truck, the truck may be directed to the centralized processing facility. If the mobile storage tank is mounted to or mounted within a skid, trailer or shipping container, the skid, trailer or shipping container may be loaded directly onto or otherwise coupled to the mode of transportation (e.g., a vehicle such as a truck, ship, rail car) for transport to the centralized processing facility. For example, a tube trailer can be temporarily parked at the pre-processing site until it is filled and/or collection is arranged, at which point it is detachably coupled to the truck tractor and transported to the centralized processing facility.

In one embodiment, compressed partially purified biogas is fed into one or more trailers (i.e., having mobile storage tanks) that are temporarily parked at the pre-processing site. Once the trailers are filled to the desired level, which may for example take between 1.5 and 3 hours, they may be coupled to a truck (e.g., the same truck or different trucks) and transported to the centralized processing facility.

In one embodiment, compressed partially purified biogas is fed into one or more trucks (i.e., having mobile storage tanks) that are temporarily parked at the pre-processing site. Once the trucks are filled substantially to full capacity or otherwise to the desired level, which may, for example, take several hours (e.g., about 1.5 to about 3 hours), they may be transported directly to the centralized processing facility. Optionally, the mobile storage tanks are removably connected to the trucks.

Transporting the Partially Purified Biogas

In general, the partially purified biogas may be collected (e.g., picked-up) and transported (e.g., to the centralized processing facility). In one embodiment, the collection of partially purified biogas includes transporting the partially purified biogas at least some distance by truck, rail, or ship. In one embodiment, the transport includes moving a vessel containing the partially purified biogas by truck, rail, and/or ship at least one mile. In one embodiment, the transport includes a combination of transporting the partially purified biogas in a vessel and transporting the partially purified biogas via pipeline. Transporting the partially purified biogas as a compressed gas (e.g., at 3600 psi) is advantageous in that it increases the amount of methane delivered per tank.

In one embodiment, where the partially purified biogas is fed in one or more mobile storage tanks at the pre-processing site, once the mobile storage tanks(s) have reached a certain fill level (e.g., based on pressure or density), or a pick-up is arranged, the mobile storage tanks are transported via a truck, rail, and/or ship. For example, in one embodiment, the one or more mobile storage tanks are mounted in a shipping container that can be loaded onto a truck bed or trailer bed for transport. In one embodiment, the one or more mobile storage tanks are mounted to a trailer that can be coupled to a truck (e.g., a towing truck, a tractor unit, a leading trailer, or some prime moving vehicle) for transport.

In one embodiment, a trailer including one or more mobile storage tanks containing high pressure (e.g., 3000 psi) partially purified biogas is collected from the pre-processing site, and is then transported to the centralized processing facility. A trailer containing one or more empty mobile storage tanks (e.g., under 200 psi) is then transported back to the pre-processing site, or another pre-processing site, for exchange with a trailer containing one or more mobile storage tanks containing high pressure partially purified biogas.

In one embodiment, a single truck is provided to transport mobile storage tanks containing partially purified biogas directly to the centralized processing facility (e.g., direct route). In one embodiment, a plurality of trucks is provided to transport mobile storage tanks containing partially purified biogas directly to the centralized processing facility (e.g., direct route). In one embodiment, a plurality of trucks (e.g., tractor units) are provided to transport trailers or shipping containers containing the partially purified biogas between a plurality of pre-processing sites and the centralized processing facility. In one embodiment, a plurality of trailers containing partially purified biogas is transported by one truck (i.e., a double or triple trailer configuration). In one embodiment, the trucks are fueled by compressed natural gas (CNG). In general, the number of mobile storage tanks (e.g., trailers) temporarily associated with a pre-processing site will depend on the production rate of raw biogas and/or the distance of the pre-processing site from the centralized processing facility.

Collecting or arranging for the collection of partially purified biogas from one or more pre-processing sites advantageously can exploit the use of stationary partial purification units and mobile storage tanks. Accordingly, the process/system is more efficient. For example, since the partially purified biogas is produced by a stationary partial purification unit, collection (e.g., pick-up) of the partially purified biogas can be more expedient as most or all of the partially purified biogas can be produced before the pick-up. Even in embodiments where the partially purified biogas is generated during pick-up, the use of the stationary partial purification unit is advantageous. For example, the use of a stationary partial purification unit can allow the raw biogas to be at least partially purified using a unit customized for the quantity and quality of raw biogas provided at the corresponding pre-processing site. Moreover, it can efficiently remove toxic gases from the raw biogas (e.g., $H_2S$) so that the biogas collection system does not have to address transportation concerns related to the same.

Once transported, the partially purified biogas can be decompressed and removed from the mobile storage tank(s). For example, in one embodiment, a centralized decompression unit is provided on a manifold that receives partially purified biogas from different mobile storage tanks. Advantageously, transporting the partially purified biogas in mobile storage tanks may obviate the need for dedicated buffer storage at the centralized processing facility. For example, since the partially purified biogas is transported in mobile storage tanks, the partially purified biogas can be stored therein until required. Moreover, since the partially purified biogas may be transported at high pressure, this higher pressure may be exploited during the processing process.

In some cases, challenges may arise when the partially purified biogas contains a significant amount of $CO_2$ and/or is stored at high pressure. For example, there may be issues with freezing of the lines as $CO_2$ gas could form dry ice upon depressurization. In one embodiment, problems associated with $CO_2$ freezing are minimized or avoided by using the heat generated during compression for filling the mobile pressure tank to maintain the partially stored biogas at an increased temperature so that, upon expansion, it does not freeze. Advantageously, this also reduces the amount of energy required to cool the gas after it is compressed. In another embodiment, problems associated with $CO_2$ freezing are addressed by heating the compressed gas before it is depressurized (e.g., at the receiving end). Advantageously, this allows more partially purified biogas to be stored. In another embodiment, problems associated with $CO_2$ freezing are addressed by displacing the partially purified gas by feeding an alternate fluid into the vessels that has less propensity to freeze. In one embodiment, this fluid is a cleaner gas (e.g. relatively pure methane). In one embodiment, the fluid is a liquid, which pushes the partially purified biogas out to another location. In one embodiment, the partially purified gas is displaced using a positive displacement process (e.g., a piston type of mechanism). In some embodiments, the raw biogas is not subject to a partial purification and is transported to the centralized processing facility according to one of the embodiments described herein.

Centralized Processing

In general, the raw or partially purified biogas transported to the centralized processing facility will be used to produce a chemical or fuel (e.g., a renewable chemical or fuel) 50 using any suitable technology.

In one embodiment, the centralized processing facility produces RNG. The RNG can be used as a substitute for fossil natural gas, can be injected into the natural gas grid, and/or can be used as a transportation fuel. In embodiments where the RNG is injected into the natural gas grid, it may be withdrawn at another location for use as a fuel (e.g., transportation fuel), or may be withdrawn at a fuel production facility in order to produce a fuel (e.g., a renewable fuel or a fuel having renewable content). For purposes herein, the term "renewable natural gas" or "RNG" refers to biogas that has been upgraded to meet or exceed applicable natural gas pipeline quality standards and/or specifications, meet or exceed applicable quality specifications for vehicle use (e.g., CNG specifications), and/or that qualifies as RNG under applicable regulations. Pipeline specifications include specifications required for biogas for injection into a natural gas commercial distribution system. Pipeline quality standards or specifications may vary by region and/or country in terms of value and units. For example, pipelines standards may require the RNG to have a $CH_4$ level that is greater than 95%. In addition, or alternatively, the natural gas pipeline standards may refer to the purity of the gas expressed as a heating value (e.g., in British Thermal Units (BTU)/standard cubic foot). Pipeline standards may require, for example, that the heating value of RNG be greater than about 950 BTU/scf, greater than about 960 BTU/scf, or greater than about 967 BTU/scf. In the United States (US), RNG and CNG standards may vary across the country. For example, for one company, the pipeline specifications may require a heating value between 967 and 1110 BTU/scf, a $CO_2$ content less than 1.25%, an $O_2$ content less than 0.02%, a total inert content (e.g., $CO_2$, $N_2$, helium, argon, neon) less than 4%, an $H_2S$ concentration less than 0.25 gr/100 scf of gas, and a water concentration less than 7 lbs/MMscf. Whereas for another company, the pipeline specifications may require a heating value greater than 970 BTU/scf, a $CO_2$ content less than 1.4%, an $O_2$ concentration less than 10 ppm, an $N_2$ content less than 1.2%, and $H_2S$ concentration less than 1 ppm. The specifications for CNG for vehicle use may include a heating value between 940-1100 BTU/scf, a $CO_2$+ $N_2$ content less than about 4%, an $O_2$ content less than 1%, and a $H_2S$ content less than 6 ppm(v).

In one embodiment, the centralized processing facility includes a biogas upgrading system and/or is a biogas upgrading facility (e.g., for producing RNG). In one embodiment, the centralized processing facility is a centralized biogas upgrading facility. The centralized biogas upgrading facility may be an independent facility or may be integrated with a biogas production plant. For example, in one embodiment, the centralized biogas upgrading facility is located at or near a landfill site. Advantageously, this configuration can provide higher quality RNG at a reduced capital cost (e.g., relative to a plurality of biogas upgrading facilities). Moreover, since there are higher volumes fed into the centralized biogas upgrading facility (e.g., it receives raw biogas and/or partially purified biogas from a plurality of sources), the biogas upgrading benefits from the economies of scale (e.g., the capital cost of biogas upgrading systems are subject to economies of scale, where smaller plants are less capital efficient than larger plants).

In one embodiment, the centralized biogas upgrading facility receives biogas (e.g., raw and/or partially purified) at a rate greater than 2000 SCFM (standard cubic feet per minute). In one embodiment, the centralized biogas upgrading facility receives biogas at a rate greater than 4,000 SCFM. In one embodiment the centralized biogas upgrading facility receives biogas at a rate greater than 5,000 SCFM. In one embodiment the centralized biogas upgrading facility receives biogas at a rate greater than 6,000 SCFM. In one embodiment the centralized biogas upgrading facility receives biogas at a rate greater than 8,000 SCFM. In one embodiment the centralized biogas upgrading facility receives biogas at a rate greater than 10,000 SCFM. In one embodiment the centralized biogas upgrading facility receives biogas at a rate greater than 15,000 SCFM. In one embodiment the centralized biogas upgrading facility receives biogas at a rate between 10,000 and 20,000 SCFM.

In one embodiment, the centralized biogas upgrading facility is a stand-alone facility located near a natural gas pipeline and receives partially purified biogas transported from one or more biogas sources (e.g., landfill or anaerobic digester).

In general, the biogas upgrading system and/or the biogas upgrading facility may include one or more units and/or stages that remove non-methane components from the biogas (e.g., $CO_2$, $N_2$, $H_2O$, $H_2S$, $O_2$, $NH_3$, VOCs, siloxanes, and/or particulates). These non-methane components may be removed by any combination of chemical and/or physical technologies, in one or more stages. For example, one stage may remove more than one non-methane component. The removal of $H_2O$, $H_2S$, $O_2$, $NH_3$, VOCs, siloxanes, and/or particulates may be referred to as biogas cleaning.

In one embodiment, the biogas upgrading system and/or facility includes one or more purification units known in the art for cleaning and/or upgrading biogas. For example, $H_2O$ may be removed using a standard biogas dehumidifier, whereas $H_2S$ may be removed using a commercial $H_2S$ removal unit (e.g., based on activated carbon, molecular sieve, iron sponge, water scrubbing, NaOH washing, and/or biofilter or biotrickling filter technologies). Some $H_2S$ may also be removed during the water removal step, if present. $O_2$ may be removed by catalytic oxidation, membranes, or low pressure PSA. $CO_2$ may be removed by absorption (e.g., water scrubbing, organic physical scrubbing, chemical scrubbing), pressure swing adsorption (PSA), membrane permeation, and/or cryogenic upgrading.

In conventional biogas upgrading, the non-methane (e.g., $CO_2$, $H_2S$, $H_2O$, $N_2$, $O_2$, VOCs, and/or siloxane) removal systems may be selected in dependence upon the source of the biogas, the non-methane components present, the desired purity, the capacity of the system, and other cleaning systems present, as would be understood by a person skilled in the art. For example, since each biogas source is unique, the biogas upgrading technology, configuration, and sizing of the system components may be selected in dependence upon the specific situation. However, it can be challenging to determine the best biogas upgrading technology when the carbon dioxide levels and/or biogas production levels (e.g., flow rates) vary with time. With centralized processing, the biogas upgrading system advantageously can be designed to upgrade biogas from a number of different sources, and thus may provide a higher quality RNG and/or the flexibility to adjust to a varying biogas production (e.g., flow rates). For example, in some instances it may not be economically justifiable to provide $N_2$ removal for a small-scale biogas upgrading system (e.g., either stationary or mobile). However, by collecting and transporting partially purified biogas to a centralized processing facility with $N_2$ removal, a higher $CH_4$ content can be achieved.

In one particularly advantageous embodiment, the partial purification system used at the pre-processing site is used to remove $CO_2$, but little to no $N_2$, while the centralized processing facility includes $N_2$ removal. For example, in one embodiment, the partial purification uses a membrane system to separate $CO_2$ and $CH_4$, while $N_2$ removal is achieved at the centralized processing facility using a different technology and/or type of membrane. For example, PSA technology is efficient at removing $N_2$ from biogas.

In one embodiment, the centralized processing facility produces a chemical and/or fuel other than RNG. In one embodiment, the centralized processing facility is a fuel production facility. In this embodiment, the fuel production facility may or may not include a biogas upgrading system. In one embodiment, the fuel production facility includes a biogas upgrading system. For example, in one embodiment, the centralized processing facility includes a biogas upgrading system for removing one or more impurities prior to or as part of a fuel production process (e.g., produces RNG for use as a feedstock for the fuel production).

In one embodiment, the centralized processing facility produces RNG (e.g., compressed RNG (bio-CNG) or liquefied RNG (bio-LNG)) that is transported (e.g., via a natural gas distribution system, truck, rail, ship) to a fuel production facility to produce the fuel.

In one embodiment, RNG produced at the centralized processing facility is transported to the fuel production facility using a natural gas distribution system. In this embodiment, the RNG may be delivered as a fungible batch. When RNG is delivered as a fungible batch, RNG is injected into the distribution system, and an equivalent amount of gas (i.e., measured in MMBTU) is withdrawn from the distribution system (e.g., at a different location). Since many natural gas distribution systems may recognize the transfer or allocation of the environmental attributes of RNG injected into the distribution system to gas withdrawn at a different location, the withdrawn gas may be considered RNG. In general, the transfer is made on a displacement basis, where transactions within the distribution system involve a matching and balancing of inputs and outputs. Typically the direction of the physical flow of gas is not considered.

In one embodiment, RNG produced at the centralized processing facility is transported to the fuel production facility as bio-CNG, by rail car, ship, or truck.

In one embodiment, RNG produced at the centralized processing facility is transported to the fuel production facility as bio-LNG, by rail car, ship, or truck. In one embodiment, the biogas (i.e., raw or partially purified) is upgraded to RNG at the centralized processing facility using cryogenic biogas upgrading technology. Advantageously, using cryogenic biogas upgrading can produce bio-LNG directly. In addition, it may provide liquefied bio-$CO_2$, which in one embodiment, is provided as a co-product. In one embodiment, the transported bio-LNG is re-gasified and used to produce the fuel.

Advantageously, using the biogas-derived methane (e.g., raw biogas, partially purified biogas, or RNG) as a feedstock for the fuel production process (e.g., at the centralized processing facility or a separate fuel production facility) may produce a fuel that is renewable or has renewable content. The terms "biogas-derived methane" and "methane derived from biogas", as used herein, refers to methane obtained from biogas and/or to methane withdrawn from a fungible distribution system into which methane obtained from biogas is injected, where the withdrawn methane is recognized as possessing the environmental attributes of the injected methane.

In one embodiment, the fuel production process produces hydrogen, methanol, ethanol, gasoline, diesel, and/or dimethyl ether (DME). In one embodiment, the fuel production process uses raw biogas, partially purified biogas, RNG, or any combination thereof, as a feedstock to produce hydrogen, methanol, ethanol, gasoline, diesel, and/or dimethyl ether (DME).

In one embodiment, the fuel production process produces a fuel using one-step conversion process (e.g., partial oxidation of methane to methanol).

In one embodiment, the fuel production process produces the fuel using a multiple-step conversion process based on a syngas intermediate. Syngas, which is a mixture including CO, $CO_2$, $H_2$, may be formed by subjecting methane to methane reforming (e.g., steam methane reforming (SMR), autothermal reforming (ATR), dry methane reforming (DMR), or partial oxidation (POX)). In one embodiment, the feedstock for the methane reforming is a gas stream containing biogas-derived methane. For example, in one embodiment, the feedstock for the methane reforming is partially purified biogas or RNG. In one embodiment, the feedstock for the methane reforming is a gas stream including raw biogas, partially purified biogas, and/or RNG. Advantageously, using a gas containing biogas-derived methane as a feedstock for methane reforming produces a biogas-derived syngas, which may be used in any number of fuel production processes. Advantageously, the biogas-derived syngas contains biogenic carbon, which in one embodiment, is used to produce the fuel. The term "biogenic", as used herein, refers to being sourced directly or indirectly from non-fossil organic material.

In one embodiment, a gas stream comprising the biogas-derived methane is subjected to a SMR reaction to produce syngas. For example, in one embodiment, a gas stream containing raw biogas, partially purified biogas, and/or RNG is fed into a reformer configured to support the following reaction:

$$CH_4 + H_2O + heat \rightarrow CO + 3H_2 \quad (1)$$

In general, the SMR reaction uses a catalyst. Without being limiting, the catalyst may be nickel-based. Optionally, the catalyst is supported on a support of suitable material (e.g., alumina, etc.) Optionally, promoters (e.g., MgO) are added. Without being limiting, conventional steam reforming units may operate at pressures between 200 and 600 psi and temperatures between about 450 to 1000° C.

In one embodiment, a gas stream comprising the biogas-derived methane is subjected to a POX reaction to produce syngas. For example, in one embodiment, a gas stream containing raw biogas, partially purified biogas, and/or RNG is fed into a reformer configured to support the following reaction:

$$CH_4 + \tfrac{1}{2} O_2 \rightarrow CO + 2H_2 + heat \quad (2)$$

POX reactions, which include thermal partial oxidation reactions (TPOX) and catalytic partial oxidation reactions (CPOX), are so called because they lack the stoichiometric amount of oxygen required to completely oxidize the hydrocarbons to $CO_2$. POX also may be referred to as oxidative reforming. In addition to hydrogen and carbon monoxide, the product gas may also contain nitrogen if the reaction is carried out with air rather than pure oxygen and/or a relatively small amount of $CO_2$ and/or other compounds. In general, TPOX is mildly exothermic, and therefore does not have the fuel demand required for SMR. Without being limiting, TPOX reactors may operate at pressures between 430 and 1000 psi and temperatures between about 1200 to 1500° C.

In one embodiment, a gas stream comprising the biogas-derived methane is subjected to a DMR reaction to produce syngas. For example, in one embodiment, a gas stream containing raw biogas, partially purified biogas, and/or RNG is fed into a reformer configured to support the following reaction:

$$CO_2 + CH_4 \rightarrow 2CO + 2H_2 \quad (3)$$

Without being limiting, the DMR catalyst may be iron, ruthenium, palladium, or platinum based.

In one embodiment, a gas stream comprising the biogas-derived methane is subjected to an ATR reaction to produce syngas. For example, in one embodiment, a gas stream containing raw biogas, partially purified biogas, and/or RNG is fed into a reformer configured to support one of the following reactions:

$$4CH_4 + O_2 + 2H_2O \rightarrow 10H_2 + 4CO \quad (4)$$

$$2CH_4 + O_2 + CO_2 \rightarrow 3H_2 + 3CO + H_2O \quad (5)$$

In general, ATR combines partial oxidation with the catalytic steam reforming of methane (Eq. 4), or combines partial oxidation with the catalytic dry reforming of methane (Eq. 5), in a single reactor. Heat generated from the partial oxidation (e.g., in the combustion zone of the reactor) may be used in the catalytic reforming (e.g., in the reforming zone of the reactor). Accordingly, a stand-alone ATR advantageously may not require the supply or dissipation of thermal energy. Without being limiting, conventional ATR reactors may operate at temperatures between about 750 to 1400° C.

In general, the selected methane reforming reaction and/or process parameters determine the hydrogen to carbon monoxide ratio ($H_2$:CO) achieved in the syngas produced. In SMR, process parameters such as the steam to carbon ratio (S:C) in feed, reactor pressure, and exit temperature, may affect the $H_2$:CO ratio. ATR uses a lower S:C ratio in the reformer feed as compared to SMR. Such lower S:C ratios may produce a syngas with a lower $H_2$:CO ratio.

In these embodiments, the gas stream subjected to the methane reforming may be primarily methane (e.g., RNG) or may contain one or more other components in an amount sufficient for the heating value to be less than 950 BTU/scf. For example, although it may be advantageous to remove most of the $H_2S$, which may poison some catalysts if present, methane reforming processes can be tolerant to some $N_2$ and/or $CO_2$. For example, as illustrated above, the DMR reaction and some ATR reactions use $CO_2$. With regard to SMR, the presence of excess $CO_2$ in the feed may make the system sensitive to carbon formation in the operation regime, which could deposit on the support, as well as on the active phase of the catalyst. In one embodiment, an excess of steam is fed into the SMR reactor, which may suppress carbon formation.

Since the methane reforming process may be tolerant to some $N_2$ and/or $CO_2$, the process of partially purifying biogas from a plurality of biogas sources, and transporting the partially purified biogas to the centralized processing facility (e.g., fuel production facility) may be particularly advantageous. For example, in one embodiment, where the partial purification removes at least 75%, at least 80%, at least 85%, at least 90%, or at least 95% of the $CO_2$ from the raw biogas, the partially purified biogas may be compressed and transported more economically, and more specifically, may allow more biogas-derived methane to be transported to the centralized processing facility (e.g., fuel production facility). Depending on the partial purification (e.g., if $H_2S$ is removed), the partially purified biogas may then be fed directly into the methane reforming, without incurring the costs of purifying the biogas to RNG. In one embodiment, the gas feed to the methane reformer includes RNG and partially purified biogas, wherein the ratio of the two feeds is selected to keep the $CO_2$ content below a certain limit.

In one embodiment, the partially purified biogas is fed to a purification stage and/or pre-reformer prior to being fed to the methane reformer. A purification stage may remove sulfur, chloride, olefin, and/or other compounds that may be detrimental to the downstream reforming catalysts. Pre-reforming may allow a higher inlet feed temperature with minimal risk of carbon deposition, which may be particularly advantageous when the feed contains a significant amount of $CO_2$ (e.g., partially purified biogas).

In one embodiment, the syngas produced by the methane reformer (i.e., raw syngas) is fed to a water gas shift (WGS) reaction. In the WGS reaction, the CO in the raw syngas is reacted with water to form $CO_2$ and more $H_2$, as follows:

$$CO + H_2O \rightarrow CO_2 + H_2 + \text{small amount of heat} \quad (6)$$

Accordingly, the WGS may also affect the $H_2$:CO ratio. For example, the WGS reaction typically removes CO, while increasing $H_2$ and adding $CO_2$, thereby increasing the $H_2$:CO ratio. Feeding the raw syngas to a WGS reaction may be particularly advantageous in fuel production processes where hydrogen is produced and/or used as a feed for the fuel production process.

In general, the process may be designed such that the syngas produced in the methane reformer and/or the shifted gas produced by the WGS reaction has the $H_2$:CO ratio and/or CO:$CO_2$ ratios desired for the selected fuel production process. For example, depending on the selected technology (e.g., including the choice of microorganism), gas fermentation may require a $H_2$:CO ratio between 2:1 and 5:1, whereas Fischer-Tropsch reactions typically require a $H_2$:CO ratio close to 2:1.

In one embodiment, the reforming process (e.g., which may include one or more reforming units and/or a WGS reaction) is selected to provide an $H_2$:CO ratio that matches the fuel production process requirements. For example, stoichiometrically, the $H_2$:CO ratio of methane dry reforming is unity, while the $H_2$:CO ratio of steam reforming is about four (although in practice they may vary). Using a combination of these technologies may produce a $H_2$:CO ratio in the range suitable for the Fischer-Tropsch process or a gas fermentation.

In one embodiment, the catalysts and/or S:C ratios of the reforming reaction are selected to provide an $H_2$:CO ratio that matches the fuel production process requirements. For example, the $H_2$:CO ratio may be adjusted by adding steam or changing the reaction temperature and/or pressure.

In one embodiment, the reforming process selected does not provide a syngas having an $H_2$:CO ratio and/or CO:$CO_2$ ratio that matches the fuel production process requirements. In one embodiment, additional $H_2$ and/or $CO_2$ may be added to the syngas and/or shifted gas in order to reach the desired ratios and/or upscale the process.

In one embodiment, $H_2$ is added to the syngas or shifted gas. In one embodiment, $H_2$ is added to balance the C—H ratio. Advantageously, adding $H_2$ increases the amount of renewable carbon from the biogas incorporated into the fuel. In this embodiment, the added $H_2$ may be derived from fossil natural gas feedstock.

In one embodiment, $CO_2$ is added to the syngas and/or shifted in order to adjust the $CO:CO_2$ ratio or C—H ratio. In one embodiment, the $CO_2$ added to the syngas and/or shifted gas is biogenic. For example, in one embodiment, the $CO_2$ is obtained from a fermentation process (e.g., the $CO_2$ produced during the fermentation of corn, sugar cane, or cellulosic feedstock). In one embodiment, the $CO_2$ is obtained from biogas. In one embodiment, the $CO_2$ is obtained from a $CO_2$ removal process conducted on raw biogas or partially purified biogas used as a feedstock for part of the fuel production process.

As will be recognized by those skilled in the art, the desired $H_2:CO$ ratio and/or $CO:CO_2$ ratios may be dependent on selected fuel production process, including any catalysts or microorganisms used therein. Advantageously, the CO and $H_2$ formed in the methane reforming reactions and/or the $CO_2$ and/or $H_2$ formed in the WGS reaction are derived from the $CH_4$ in the biogas. Accordingly, fuel produced from the syngas and/or shifted gas may be renewable, have renewable content, and/or have a reduced carbon intensity (CI).

In one embodiment, the fuel production process produces $H_2$. In one embodiment, $H_2$ is produced by subjecting biogas-derived methane to an SMR reaction to produce syngas, which is subject to a water gas shift reaction (WGS) to increase the concentration of the $H_2$, followed by a hydrogen purification (e.g., pressure swing adsorption (PSA) or membrane) to purify the $H_2$. In one embodiment, the purified $H_2$ is used directly as a fuel (e.g., a transportation fuel). In one embodiment, the purified $H_2$, which may be referred to as renewable $H_2$, is incorporated into a crude-oil derived liquid hydrocarbon to produce gasoline and/or diesel having renewable content (e.g., see U.S. Pat. Nos. 8,658,026, 8,753,854, 8,945,373, 9,040,271, 10,093,540).

In one embodiment, the fuel production process produces methanol. Methanol may be formed in a methane-to-methanol process. For example, in one embodiment, the fuel production process produces methanol from biogas-derived methane using Imperial Chemical Industries (ICI) low pressure methanol (LPM) process, Katalco low pressure methanol process, Lurgi low pressure methanol process, Haldor-Topsoe process, or liquid process such as the liquid-phase methanol synthesis process (LPMeOH). Suitable catalysts may include copper, zinc, oxide, alumina, chromium oxide, or combinations thereof. Methanol may be used as a fuel (e.g., marine fuel), may be blended with gasoline, may be used in a methanol-to-olefins process, may be used to produce dimethyl ether (DME), may be used to produce methyl tertiary butyl ether (MTBE), may be used to produce biodiesel, or may be used in a methanol-to-gasoline (MTG) process. In one embodiment, the fuel production process produces DME, MTBE, biodiesel, or gasoline from biogas-derived methanol.

In one embodiment, the fuel production process produces ethanol. Ethanol may be formed by gas fermentation of syngas with anaerobic microorganisms. Ethanol may be used as a fuel or may be blended with gasoline. In one embodiment, the fuel production process produces ethanol by the gas fermentation of syngas produced by methane reforming of biogas-derived methane. The production of ethanol by the gas fermentation of syngas with anaerobic microorganisms is well known e.g., see U.S. Pat. No. 10,202,622).

In one embodiment, the fuel production process produces gasoline. Gasoline may be produced by converting syngas to methanol, which is transformed into gasoline (e.g., a methanol-to-gasoline (MTG) process). In one embodiment, the fuel production process produces gasoline from biogas-derived syngas.

In one embodiment, the fuel production process produces diesel. Diesel may be produced using a gas-to-liquid (GTL) refinery process where methane is converted to longer-chain hydrocarbons via a syngas intermediate. For example, diesel may be produced using a Fisher-Tropsch type process. Alternatively, diesel may be produced by incorporating renewable hydrogen into a crude-oil derived liquid hydrocarbon, where the resulting diesel has renewable content. In one embodiment, the fuel production process produces diesel from biogas-derived syngas.

In one embodiment, the fuel production process produces DME. DME may be produced by catalytic dehydration of methanol. DME may be used as a fuel for diesel engines (e.g., a clean diesel alternative). In one embodiment, the fuel production process produces DME.

In each of the above described chemical or fuel production processes that use methane as a feedstock, the feedstock may be entirely derived from biogas or may be a combination of fossil based methane and biogas-derived methane. For example, in one embodiment, the fuel production facility is designed to produce the chemical and/or fuel using a fossil feedstock (e.g., fossil methane). In this embodiment, the fuel production facility may be provided with a receiving station and biogas upgrading system in order to also use a biogas-derived methane as a feedstock, or may use RNG provided as a fungible batch.

While the feedstock may contain a combination of fossil-based methane and biogas-derived methane, one significant advantage of arranging for the transport of partially purified biogas from a plurality of biogas sources is that the economics of producing the fuel from biogas-derived methane (i.e., with no fossil methane in the feedstock) is improved and/or becomes feasible.

In one embodiment, biogas from a plurality of biogas sources is aggregated, thereby improving consistency of the process by averaging out the $CO_2/CH_4$ ratios, flow rates, and/or other variables. In addition, it may dilute impurities, thereby improving the upgrading and/or fuel production process. Advantageously, collecting an aggregate of gas is advantageous because biogas upgrading and/or fuel production can benefit from economies of scale.

In one embodiment, the partially purified biogas transported to the centralized processing facility is processed as an aggregate of gases. For example, in one embodiment, the partially purified biogas transported from a first pre-processing site is combined with partially purified biogas transported from a second other pre-processing site. In one embodiment, the partially purified biogas transported from a first pre-processing site is combined with raw biogas from another source.

In one embodiment, the partially purified biogas transported from a first pre-processing site is combined with partially purified biogas transported from a second other pre-processing site within a receiving manifold, prior to any further purification and/or fuel production. In one embodiment, the partially purified biogas transported from a first pre-processing site is combined with biogas (e.g., raw or partially purified) at a later stage within the upgrading process or fuel production process. For example, in one particularly advantageous embodiment, the partially purified biogas transported from a first pre-processing site is combined with other biogas (e.g., raw or partially purified) at a stage in the upgrading process and/or fuel production process selected in dependence upon the type and level of partial purification provided at the first pre-processing site.

In one embodiment, the partially purified biogas transported from a first pre-processing site is combined with other biogas (e.g., raw or partially purified) prior to any further purification of the partially purified biogas. In one embodiment, the partially purified biogas transported from a first pre-processing site is combined with other biogas (e.g., raw or partially purified) early in the biogas upgrading process (e.g., before or after $H_2S$ and/or $H_2O$ removal, but prior to $CO_2$ removal). In one embodiment, the partially purified biogas transported from a first pre-processing site is combined with other biogas (e.g., raw or partially purified) later in the biogas upgrading process (e.g., after $CO_2$ removal).

In one embodiment, the fuel is provided to another party. For example, in one embodiment, the fuel is RNG, and the RNG is injected into a distribution system, where it is withdrawn at another location for use as a transportation fuel. In one embodiment, the fuel is RNG, and the RNG is compressed and provided to a CNG refilling station. In one embodiment, the fuel is RNG, and the RNG is liquefied and provided for use as a transportation fuel. In general, bio-CNG and/or bio-LNG can be transported to an off-grid industrial site and/or provided to a filling station for use in transportation.

In one embodiment, a fuel credit or renewable energy credit associated with the biogas and/or fuel produced is generated or caused to be generated. The term "cause" or "causing", as used herein, refers to arranging or bringing about a specific result (e.g., a withdrawal of a gas from a distribution system), either directly or indirectly, or playing a role in a series of activities through commercial arrangements such as a written agreement, verbal agreement, or contract.

The term "credit", "renewable fuel credit", or "fuel credit", as used herein, refers to any rights, credits, revenues, offsets, greenhouse gas rights, or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract, or otherwise. The renewable fuel credit may be a certificate, record, serial number or guarantee, in any form, including electronic, which evidences production of a quantity of fuel meeting certain life cycle GHG emission reductions relative to a baseline (e.g., a gasoline baseline) set by a government authority.

The generation of fuel credits or renewable energy credit associated with the biogas and/or fuel may be related to the environmental attributes thereof and/or the corresponding life cycle GHG emission emissions. To determine life cycle GHG emissions associated with a fuel, analyses are conducted to calculate the GHG emissions related to the production and use of the fuel throughout its life cycle. Life cycle GHG emissions include the aggregate quantity of GHG emissions related to the full life cycle of the fuel, including all stages of fuel and feedstock production and distribution, from feedstock generation or extraction, through the distribution and delivery, and use of the finished fuel to the ultimate consumer. GHG emissions typically account for total net GHG emissions, both direct and indirect, associated with feedstock production and distribution, the fuel production, and distribution and use.

In one embodiment, the fuel produced is a transportation fuel, and a fuel credit is generated or is caused to be generated. Fuel credits, such as Renewable Identification Numbers (RINs) under the US Environmental Protection Agency (EPA) Renewable Fuel Standard, or carbon credits under state supported low carbon fuel standards, can be lucrative.

In one embodiment, the transportation fuel and/or renewable content has life cycle GHG emissions that are at least 20% less than the life cycle GHG emissions of a gasoline baseline using EPA methodology, preferably at least 50% or 60% less.

Description of Various Embodiments

FIG. 3a shows a system in accordance with one embodiment. The system includes a plurality of pre-processing sites $30a_i$, $30a_{ii}$, each of which includes a source of raw biogas $10a$ (e.g., feed from landfill, anaerobic digester, and/or biogas pipeline) and a partial purification system $20a$ (i.e., for removing $H_2O$, $H_2S$, and/or $CO_2$ from the raw biogas), and optionally includes a compressor system $25a$ and/or a storage system $28a$. The system also includes a collection system $40a$ (e.g., including one or more vehicles such as a truck, ship, or rail car), for collecting and transporting the partially purified biogas produced at each biogas pre-processing site $30a_i$, $30a_{ii}$ to a centralized processing facility $50a$. The centralized processing facility includes a system $60a$ for providing a fuel (e.g., RNG).

Advantageously, since the centralized processing facility $50a$ can receive partially purified biogas from a plurality of pre-processing sites, it may be a relatively large scale facility and may profit from the economies of scale. For example, in comparison to a small-scale biogas upgrading system (e.g., farm-scale or mobile), a large-scale biogas upgrading system (e.g., >6000 SCFM) can remove more impurities (e.g., providing a methane content of at least 98%) at a reasonable cost.

Figure 3B:
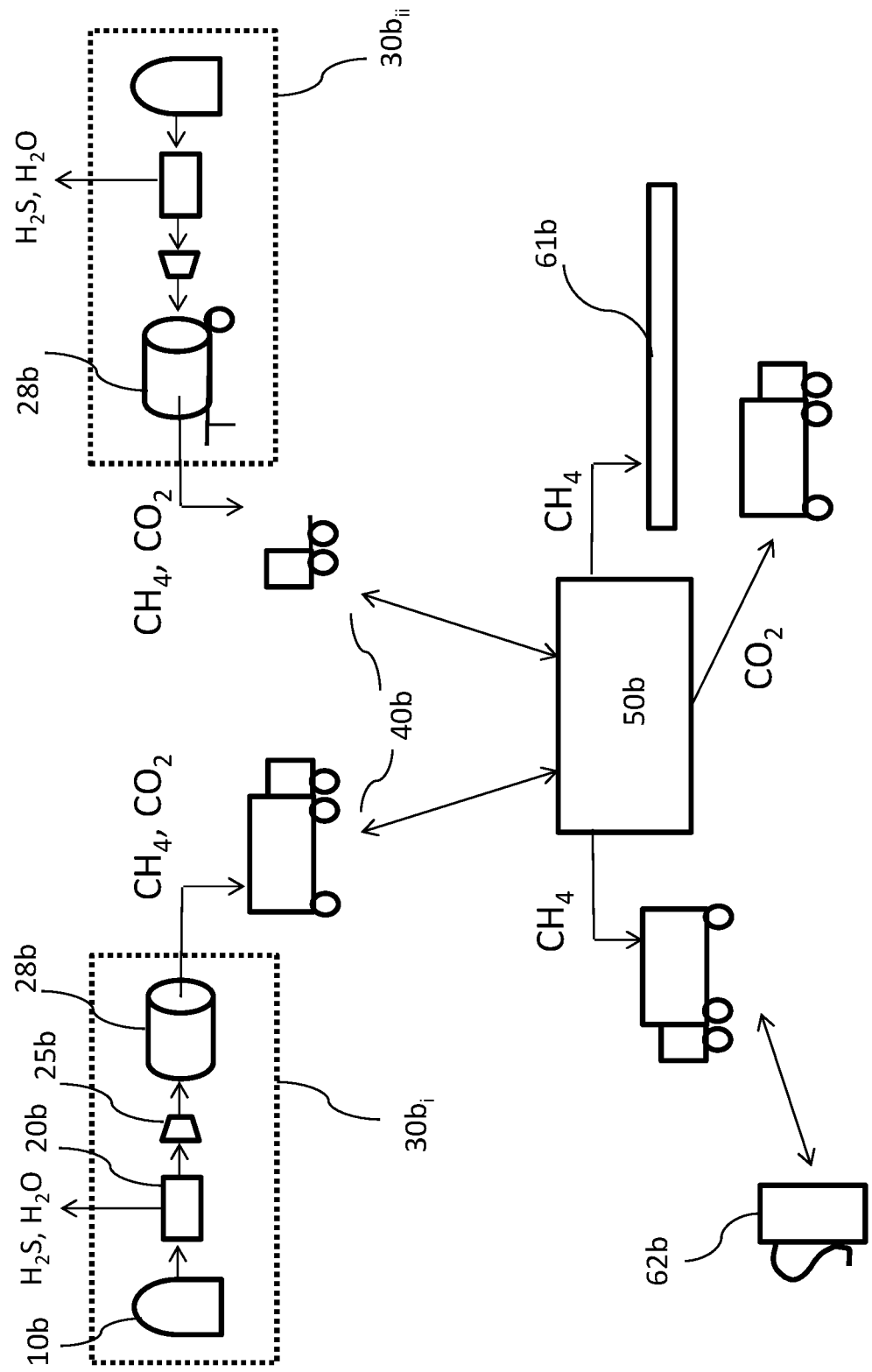
FIG. 3b is a schematic diagram showing a system for providing a fuel in accordance with another embodiment.

FIG. 3b shows a system in accordance with another embodiment. The system includes a plurality of pre-processing sites $30b_i$, $30b_{ii}$, each of which includes a source of raw biogas $10b$ (e.g., feed from landfill, anaerobic digester, and/or biogas pipeline) and a partial purification system $20b$ (i.e., for removing $H_2O$ and/or $H_2S$ from the biogas), and optionally includes a compressor system $25b$ and/or a storage system $28b$. The system also includes a collection system $40b$ (e.g., including one or more trucks, ships, or rail cars), for transporting the partially purified biogas produced at each site $30b_i$, $30b_{ii}$ to a centralized processing facility $50b$. In this embodiment, the centralized processing facility includes a biogas upgrading system that includes a system for injecting the RNG produced into a distribution system $61b$ and/or a system for transporting RNG (e.g., compressed or liquefied) to a filling station $62b$. The RNG can be used as a transportation fuel and fuel credits may be generated.

In this embodiment, the partial purification system $20b$ at the pre-processing sites $30b1$ and $30b_{ii}$ removes $H_2O$ and $H_2S$, but does not significantly remove $CO_2$. Accordingly, the partial purification reduces corrosion and/or other complications, but does not significantly improve compression. Rather, the $CO_2$ derived from the raw biogas is primarily removed at the centralized processing facility, where it may be vented or provided as a value-added product. This configuration is particularly advantageous when the $CO_2$ is removed by scrubbing, as such systems particularly benefit from the economies of scale.

Figure 3C:
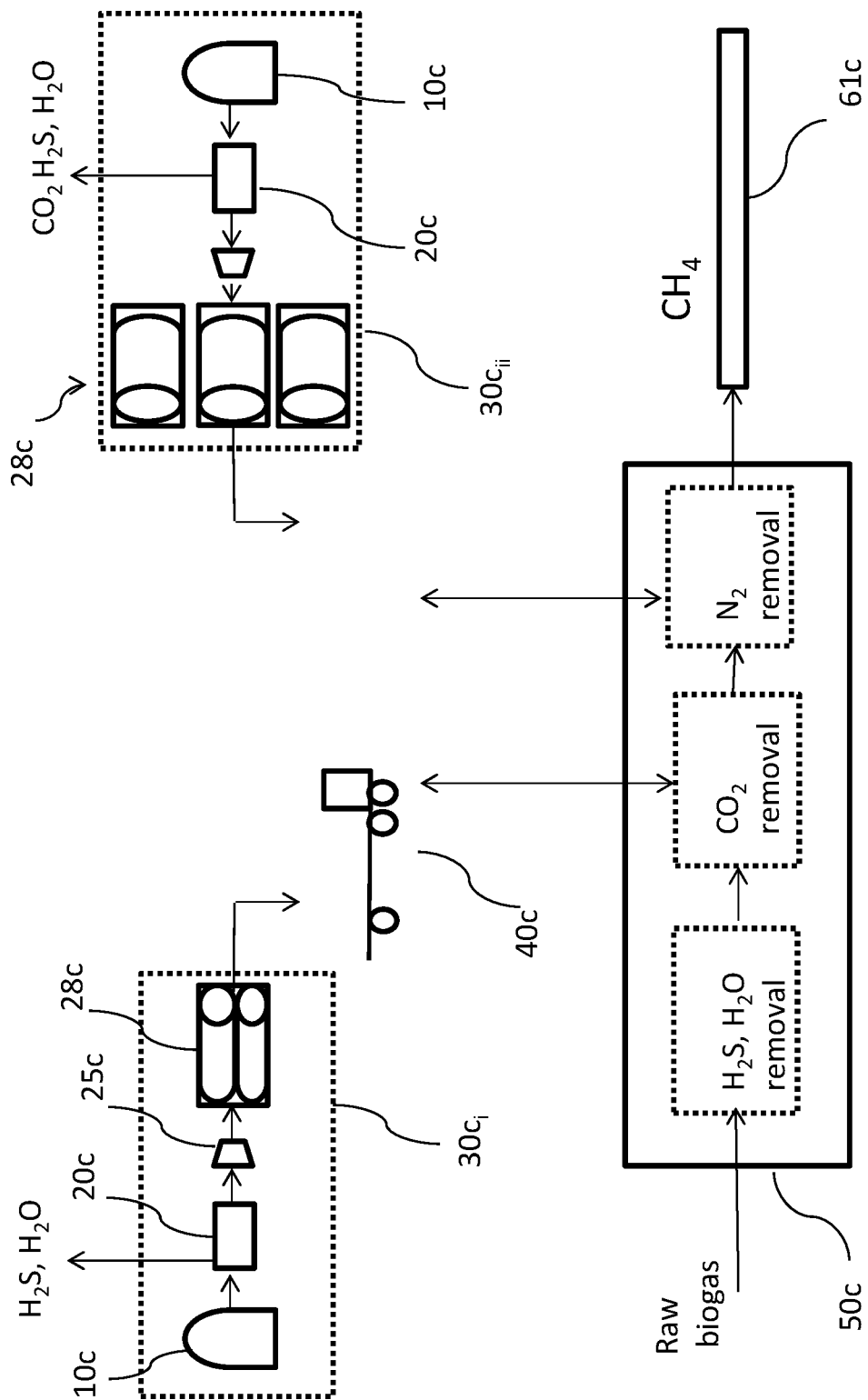
FIG. 3c is a schematic diagram showing a system for providing a fuel in accordance with another embodiment.

FIG. 3c shows a system in accordance with another embodiment. The system includes a plurality of pre-processing sites $30c_i$, $30c_{ii}$, each of which includes a source of raw biogas 10c (e.g., feed from landfill, anaerobic digester, and/or a biogas pipeline) and a partial purification system 20c (i.e., for removing $H_2O$, $H_2S$, and/or $CO_2$ from the raw biogas), and optionally includes a compressor system 25c and/or a storage system 28c. The system also includes a collection system 40c (e.g., including one or more trucks, ships, or rail cars, and optionally including a biogas pipeline), for transporting the partially purified biogas produced at each pre-processing site $30c_i$, $30c_{ii}$ to the centralized processing facility 50c. The centralized processing includes a system for 61c for providing RNG (e.g., compressed or liquefied). The RNG can be used for transportation and fuel credits generated.

In this embodiment, the partial purification system 20c at the first pre-processing site 30c, removes $H_2O$ and $H_2S$, and either removes no $CO_2$ or removes an inadequate amount of $CO_2$ to provide RNG (i.e., the resulting partially purified biogas must undergo further $CO_2$ removal to qualify as RNG). The partial purification system 20c at the second pre-processing site $30c_{ii}$ removes most of the $CO_2$ in the raw biogas, but the resulting partially purified biogas must undergo $N_2$ removal to qualify as RNG. For example, the partial purification system 20c at $30c_{ii}$ may include a membrane system or scrubbing system for removing $CO_2$ with low methane loss. In this embodiment, the partially purified biogas transported from the first pre-processing site 30c, and the partially purified biogas transported from the second pre-processing site $30c_{ii}$ are introduced into different stages of the biogas upgrading process. For example, since the partially purified biogas transported from the first pre-processing site 30c, has already been subject to $H_2O$ and/or $H_2S$ removal, but still needs the $CO_2$ content to be reduced, it is introduced downstream of the $H_2O$ and/or $H_2S$ removal stage, but upstream of or into the $CO_2$ removal stage. Since the partially purified biogas transported from the second pre-processing site $30c_{ii}$ has already been subject to adequate $CO_2$ removal, it is introduced downstream of the $CO_2$ removal stage (e.g., upstream of or into the $N_2$ removal stage).

Advantageously, this configuration enables $N_2$ to be removed from the biogas obtained at pre-processing site $30c_{ii}$ at relatively low cost (e.g., compared to using a small scale or mobile biogas upgrading system). For example, since not all biogas production plants produce enough biogas to justify investing in $N_2$ rejection, providing partial purification and transport to a centralized processing facility allows the partially purified biogas to be further polished to pipeline standards using technologies and/or a system not economically feasible on a small scale.

In this embodiment, the partially purified biogas transported from the first pre-processing site $30c_i$ is optionally combined with biogas derived from a different source prior to or during treatment in the $CO_2$ stage of the process. The partially purified biogas transported from the second pre-processing site $30c_{ii}$ is optionally combined with biogas derived from the first pre-processing site 30c, and/or biogas derived from a different source prior to or during the treatment in the $N_2$ removal stage of the process.

In addition to removing redundant steps (e.g., the partially purified biogas transported from the second pre-processing site $30c_{ii}$ is only treated to remove $CO_2$ once), this configuration may reduce compression costs and/or may improve the removal of $CO_2$. For example, consider the following. The partially purified biogas transported from the plurality of pre-processing sites $30c_i$, $30c_{ii}$ can be at a relatively high pressure (e.g., 2400-3600 psi) in these embodiments. Prior to being fed into the centralized processing system 50c, it typically will be decompressed. Early stages of the fuel production process may be designed to process raw biogas at low pressure (e.g., <10 psi), whereas later stages (e.g., $CO_2$ removal) may benefit from higher pressures (e.g., 200 psig or higher). By introducing the partially purified biogas into a stage in the process that requires and/or benefits from relatively high pressures, the decompression required for the earlier low pressure stage and subsequent recompression required for a subsequent high pressure stage is avoided. Moreover, since many $CO_2$ removal technologies, such as membrane separation, may perform better at higher pressures, this configuration may improve $CO_2$ removal.

Figure 3D:
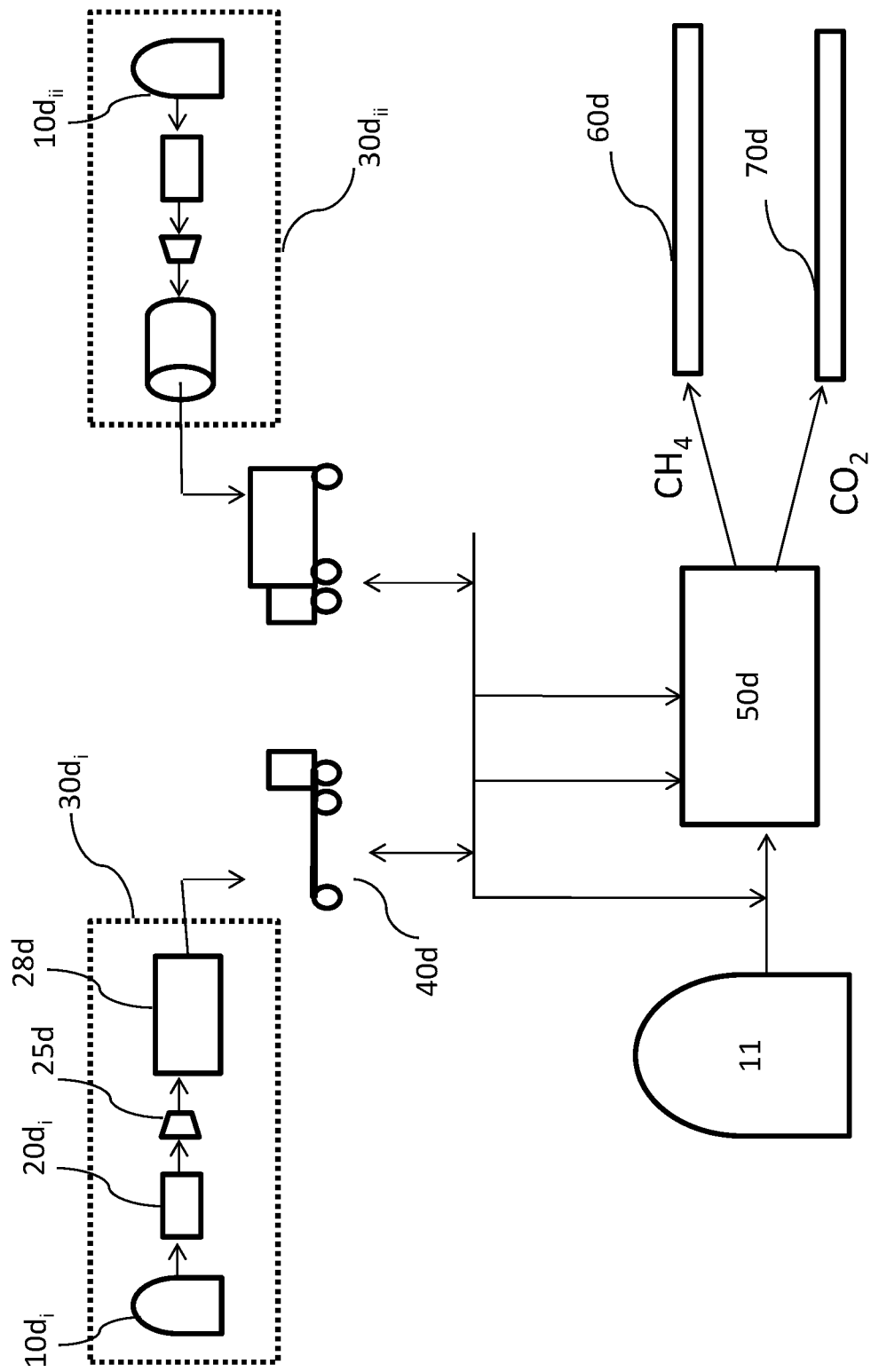
FIG. 3d is a schematic diagram showing a system for providing a fuel in accordance with another embodiment.

FIG. 3d shows a system in accordance with another embodiment. The system includes one or more pre-processing sites $30d_i$, $30d_{ii}$, each of which includes a source of biogas 10d (e.g., feed from landfill, anaerobic digester, and/or biogas pipeline) and a partial purification system 20d (i.e., for removing $H_2O$, $H_2S$, and/or $CO_2$ from the raw biogas), and optionally includes a compressor system 25d and/or a mobile storage system 28d. The system also includes a collection system 40d (e.g., including one or more trucks, ships, or rail cars, and a biogas pipeline system), for transporting the partially purified biogas produced at each pre-processing site $30d_i$, $30d_{ii}$ directly to a centralized processing facility 50d. In this embodiment, the centralized processing facility optionally includes a system for producing and distributing the RNG 60d (e.g., injection into a distribution system), and for injecting compressed $CO_2$ into a $CO_2$ pipeline system 70d.

In this embodiment, the centralized processing facility 50d is located at or near, and/or is fed raw biogas directly from, a landfill 11. In this case, the partially purified biogas collected from the one or more pre-processing biogas production sites (i.e., illustrated as two sites $30d_i$, $30d_{ii}$, but could be more or less), supplements the flow of biogas to the centralized processing system, thereby providing flexibility to adjust to varying biogas production (e.g., flow rates), and/or profiting from the economies of scale.

In this embodiment, the partially purified biogas derived from the first biogas source $10d_i$ may be combined with the partially purified biogas derived from the second source $10d_{ii}$ within the receiving manifold that feeds the biogas upgrading system 50d, and/or can be combined with biogas derived from the landfill site 11 at a selected stage in the process.

The embodiment discussed with reference to FIG. 3d is particularly advantageous. For example, since landfill sites can produce large quantities of biogas (e.g., 10,000 SCFM), the landfill can provide the primary source of biogas and/or justification for the centralized processing facility. When biogas production at the landfill varies, the number of and/or contribution from pre-processing sites may be increased.

The configurations illustrated in FIGS. 3a-3d can be particularly advantageous because, since the partially purified biogas typically will be compressed to a relatively high pressure in the mobile storage system (e.g., greater than 1000 psig), the use of processing technologies that uses higher pressures (e.g., greater than 200 psig, greater than 300 psig, greater than 400 psig, or greater than 400 psig), may be more attractive.

In one embodiment, the relatively high pressure of the partially purified biogas is exploited in the centralized biogas upgrading. For example, $CO_2$ may be removed from biogas using a two stage membrane system using an inlet pressure of about 100 psig or 200 psig. However, by using a higher inlet pressure (e.g., greater than 600 psig or greater than 800 psig), a single stage membrane can be used to remove about the same amount of $CO_2$. While it is normally challenging to justify the increased compression costs corresponding to higher pressures, particularly for biogas, since the partially purified biogas may be compressed to above 1000 psig as it fills the mobile storage system, the increased cost may be offset.

In one embodiment, the partially purified biogas is fed to a membrane system at a pressure greater than 200 psig, greater than 300 psig, greater than 400 psig, greater than 500 psig, greater than 600 psig, greater than 700 psig, or greater than 800 psig.

In one embodiment, the partially purified biogas is fed to a $CO_2$ removal that uses a liquid absorbent (e.g., water or Selexol™), which removes most of the $CO_2$ and preserves the pressure of the resulting gas stream. Depressurization of the resulting gas can cool that gas and/or gas from the landfill to create conditions for cryogenic separation of the $CH_4$ from $N_2$. In one embodiment, the biogas upgrading produces liquefied RNG (e.g., bio-LNG).

In the embodiments illustrated in FIGS. 3a to 3d, the pre-processing biogas production sites (e.g., $30a_i$, $30d_i$, $30d_{ii}$) have a partial purification system used for removing $H_2O$, $H_2S$, and/or $CO_2$ from raw biogas (e.g., leaving a non-methane content of at least 10%). Although such systems are less costly than small-scale biogas upgrading systems that provide pipeline quality upgraded biogas, it can still be an added expense for farmers and/or small scale landfills.

In accordance with one embodiment, another party (e.g., separate from the biogas producer) arranges for the provision, installation, and/or operation of the partial purification system at the pre-processing biogas production site (and optionally a plurality of other pre-processing sites), and for the collection and transport of the partially purified biogas from each pre-processing site to the centralized processing system. Accordingly, there is additional incentive for small scale biogas sources to provide the biogas for conversion to fuels (e.g., transportation fuels). In particular, this embodiment makes fuel production accessible to any small scale biogas source. More specifically, it opens up additional options for small biogas sources (e.g., individual farms) located far from a biogas grid.

Providing, installing, and/or operating a remote partial purification system, is advantageous with regard to the collection of the partially purified biogas. For example, it allows partially purified biogas to be produced prior to collection thereof, thereby improving the speed of the collection. In addition, it allows the partially purified biogas to be compressed and fed directly into a mobile storage tank, which may obviate using buffer storage and/or flaring of excess biogas, and improves the collection by allowing the transport of relatively large batches of partially purified biogas (e.g., in a hub-and-spoke configuration). For example, it is more efficient to transport one large batch directly to the biogas upgrading facility, than to provide a successive collection where smaller volumes are collected at a plurality of sites before being transported to the centralized biogas upgrading facility.

Providing, installing, and/or operating a remote partial purification system, and collecting the partially purified biogas for transport to the centralized processing facility is advantageous for the centralized processing facility in that it merits providing a larger and/or more efficient processing system. For example, for biogas upgrading, economies of scale indicate that larger plants are favored for producing higher quality gas, lower methane losses, higher plant efficiency, and higher profitability.

In the embodiments illustrated in FIGS. 3a to 3d, the centralized processing system may not only provide improved biogas upgrading, but can also provide a centralized injection into the distribution system. This is advantageous because even if upgrading to pipeline quality is economically feasible for a given situation, injection into a distribution system or a commercial fuel station may not be possible and/or may be unfavorable.

Figure 4:
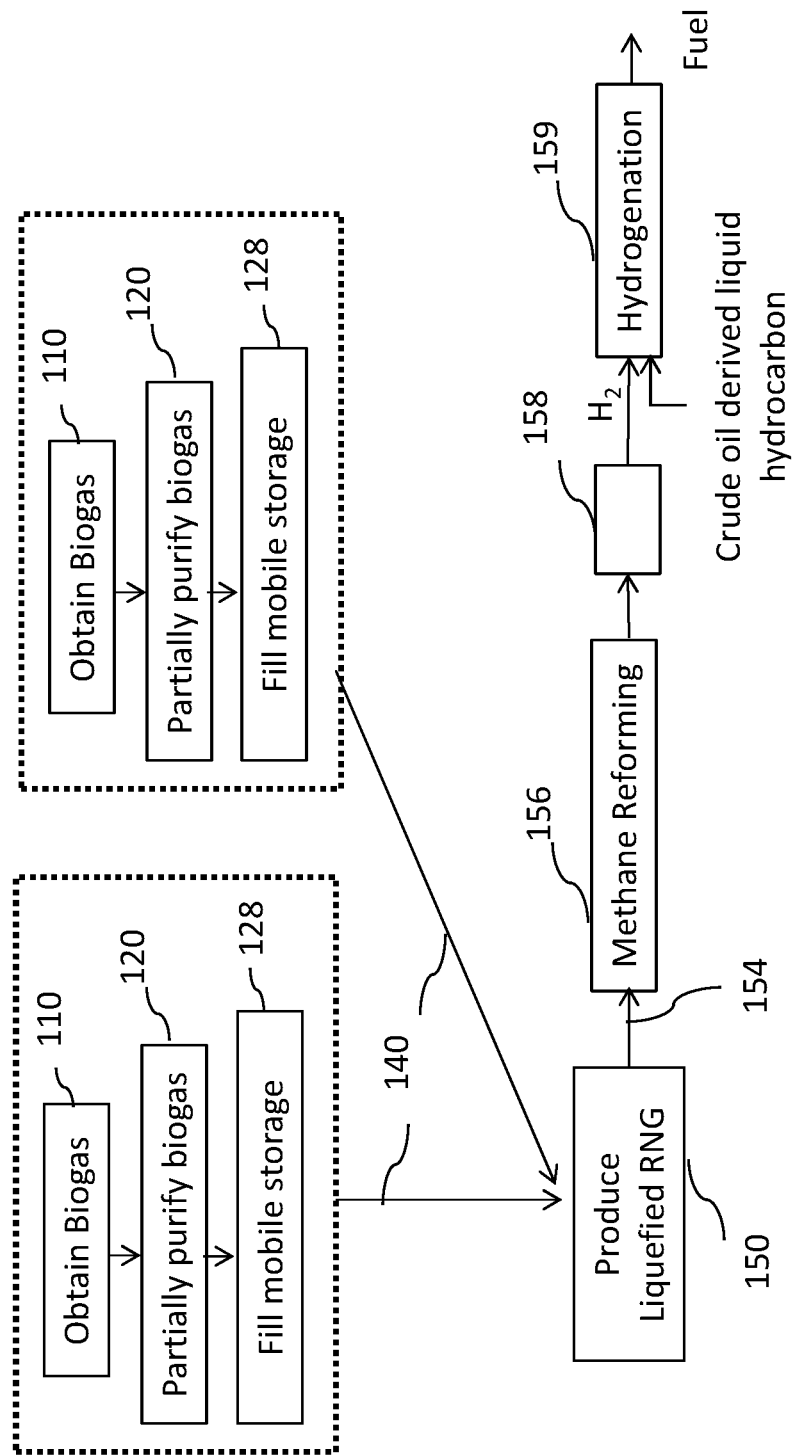
FIG. 4 is a schematic diagram showing a method for providing a liquid transportation fuel in accordance with one embodiment.

Referring to FIG. 4, there is shown a method in accordance with one embodiment of the instant invention. In this embodiment, the biogas from a plurality of biogas sources (e.g., from landfill, anaerobic digester, and/or biogas pipeline) is collected 110 at a plurality of respective pre-processing sites, wherein each biogas is subjected to a partial purification 120. In this embodiment, the partial purification removes $H_2O$, $H_2S$, and less than 85% of the $CO_2$ (e.g., in one embodiment it is less than 70%, or less than 75%). The raw biogas from each source is partially purified as it is obtained, and the partially purified biogas is compressed and fed into a mobile tank is it is produced 128. Once each mobile storage system is filled with the respective biogas, it may be transported 140 to the centralized processing facility.

At the centralized processing facility, the partially purified biogas removed from each mobile storage system is fed to one or more purification systems to produce bio-LNG 150 (e.g., in one embodiment, the purification includes a cryogenic separation). The bio-LNG is transported 154 by vehicle (e.g., truck, ship, or rail car) to a fuel production facility. At the fuel production facility, the bio-LNG is regasified and is fed to a methane reformer 156, which in this embodiment, provides an SMR reaction and a WGS reaction. The syngas produced (i.e., the shifted gas) is fed to a $H_2$ purification system 158 (e.g., PSA) to provide a stream containing renewable hydrogen. The term "renewable hydrogen", as used herein, refers to hydrogen produced using biogas-derived methane.

In this embodiment, the fuel is produced by incorporating the renewable hydrogen into a crude oil derived liquid hydrocarbon 159 in a hydrogenation reaction. By the term "crude oil derived liquid hydrocarbon", it is meant any carbon-containing material obtained and/or derived from crude oil that is liquid at standard ambient temperature and pressure. Crude oil includes liquid, gaseous, and solid carbon-containing material from geologic formations, including oil reservoirs, such as hydrocarbons found within rock formations, oil sands, or oil shale. For example, in one embodiment, the fuel production process includes using the renewable hydrogen in an oil refinery process such that the renewable hydrogen is incorporated into the fuel (e.g., see U.S. Pat. Nos. 8,658,026, 8,753,854, 8,945,373, 9,040,271, 10,093,540).

Advantageously, since the hydrogen that is added to the crude oil derived liquid hydrocarbon includes renewable hydrogen, the resultant transportation or heating fuel may be considered a partially renewable fuel, a fuel having renewable content, a fuel having reduced fossil fuel content, and/or a fuel having a reduced lifecycle GHG emissions or reduced carbon intensity (CI).

The term "carbon intensity" or "CI" means the quantity of lifecycle GHG emissions, per unit of fuel energy, expressed in grams of carbon dioxide equivalent per megajoule (gCO2e/MJ). In one embodiment, the renewable hydrogen is added to the crude oil derived liquid hydrocarbon in a reactor under conditions to hydrogenate the liquid hydrocarbon with the renewable hydrogen. In one embodiment, the renewable hydrogen is incorporated into gasoline and/or diesel.

Figure 5:
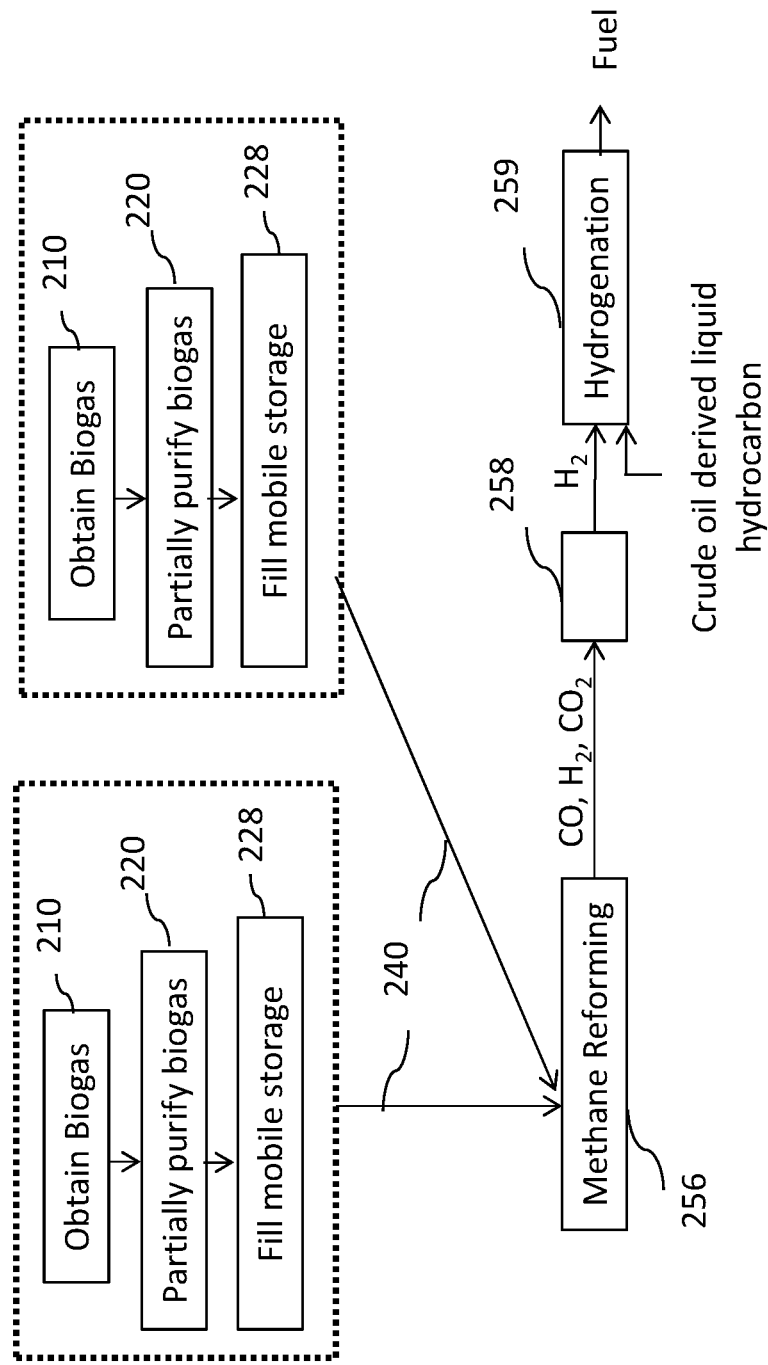
FIG. 5 is a schematic diagram showing a method for providing a liquid transportation fuel in accordance with one embodiment.

Referring to FIG. 5, there is shown a method in accordance with another embodiment of the instant invention. In this embodiment, the biogas from a plurality of biogas sources (e.g., from landfill, anaerobic digester, and/or biogas pipeline) is collected 210 at a plurality of respective pre-processing sites, wherein each biogas is subjected to a partial purification 220. In this embodiment, the partial purification removes $H_2O$, $H_2S$, and at least a portion of the $CO_2$. The raw biogas from each source is partially purified as it is obtained, and the partially purified biogas is compressed and fed into a mobile tank is it is produced 228. Once each mobile storage system is filled with biogas, the mobile storage system is transported 240 to the centralized processing facility. Advantageously, since at least a portion of the $CO_2$ has been removed, it may be favorable to transport the partially purified biogas at pressures greater than 1500 psig, greater than 2000 psig, or greater than 2500 psig.

In this embodiment, the centralized processing facility is a fuel production facility that produces a fuel from the partially purified biogases. More specifically, the centralized processing facility includes a methane reformer that produces syngas from which the fuel is produced. In this embodiment, since the partially purified biogas has had most of the $H_2O$ and $H_2S$ removed, and a portion of the $CO_2$ removed, the partially purified biogas may be fed directly into the methane reformer or may be subjected to further purification and/or pre-reforming prior to being fed into the methane reformer. The methane reformer produces syngas (e.g., raw syngas and/or shifted gas), which is fed to a $H_2$ purification system (e.g., PSA) to concentrate the renewable hydrogen. In this embodiment, it may be advantageous for the methane reformer to include an SMR reactor, which may produce more $H_2$. In one embodiment, the renewable hydrogen is provided using a pipeline system in the fuel production facility. The renewable hydrogen from the syngas is then incorporated into a crude oil derived liquid hydrocarbon 259 in a hydrogenation reaction to produce the fuel (e.g., diesel and/or gasoline).

Advantageously, since a large portion of the $CO_2$ is removed at the pre-processing site, more biogas-derived methane is provided per delivery, thereby reducing process costs. In addition, since the partial purification may provide a gas of sufficient quality for the reformer, biogas upgrading costs may be reduced. Even if the partially purified biogas is subjected to further purification at the centralized processing facility prior to being fed into the methane reformer, biogas upgrading costs may be reduced because it may not be necessary to upgrade the partially purified biogas to RNG quality. Accordingly, the cost of removing the last 5% or 10% of the $CO_2$ and/or $N_2$ from the biogas, which is generally the most challenging technically, may be avoided. In one embodiment, less than 70% of the $CO_2$ is removed. In one embodiment, less than 75% of the $CO_2$ is removed. In one embodiment, less than 85% of the $CO_2$ is removed.

Figure 6:
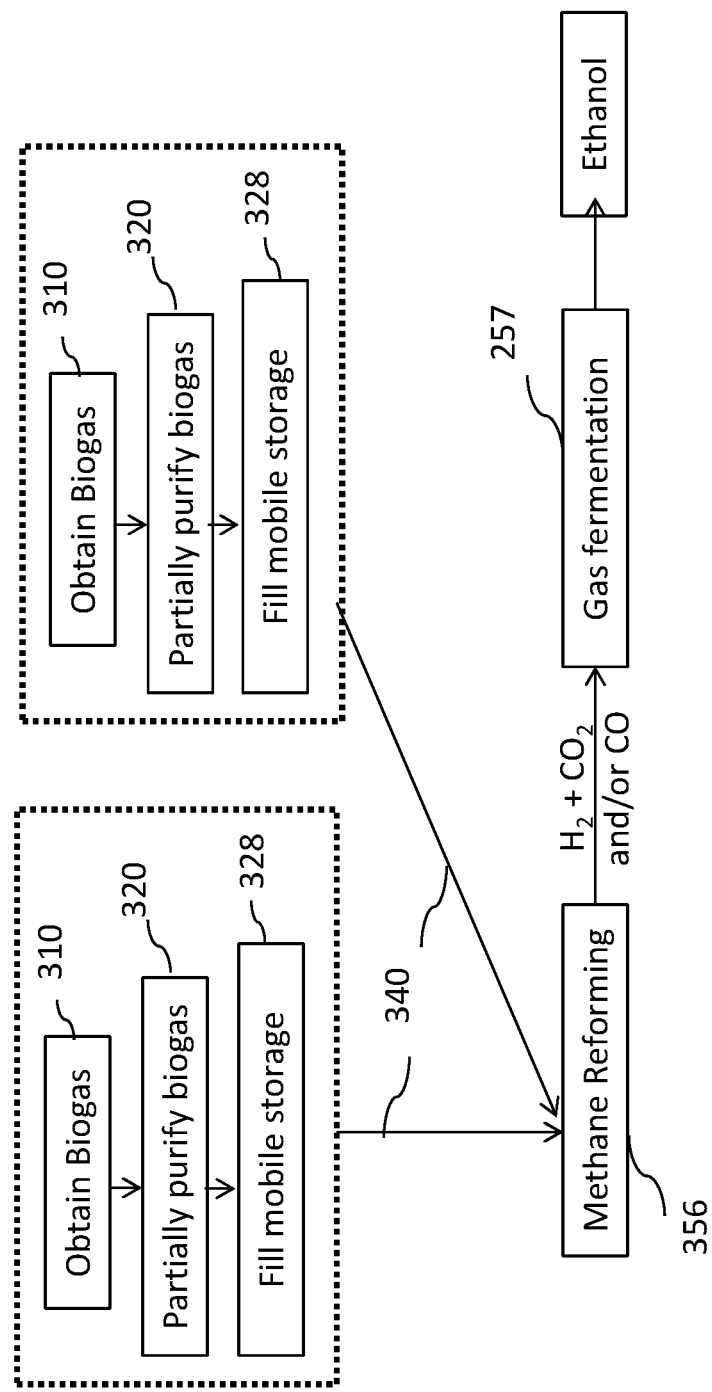
FIG. 6 is a schematic diagram showing a method for providing ethanol in accordance with one embodiment.

Referring to FIG. 6, there is shown a method in accordance with another embodiment of the instant invention. In this embodiment, the biogas from a plurality of biogas sources (e.g., from landfill, anaerobic digester, and/or biogas pipeline) is collected 310 at a plurality of respective pre-processing sites, wherein each biogas is subjected to a partial purification 320. The raw biogas from each biogas source is partially purified as it is obtained, and the partially purified biogas is compressed and fed into a mobile storage system as is it is produced 328. Once each mobile storage system is filled with biogas from one of the sources, the mobile storage system is transported 340 to the centralized processing facility.

In this embodiment, the partial purification removes $H_2O$, $H_2S$, and/or a limited amount of $CO_2$. For example, the partial purification may reduce the $CO_2$ content of the plurality of biogases from about 38% to about 20-25% (e.g., 22%). This limited $CO_2$ removal, which may reduce compression, transportation, and/or general delivery costs, advantageously may be achieved using a relatively inexpensive membrane system. Advantageously, providing no $CO_2$ removal or limited $CO_2$ removal allows $CO_2$ in the partially purified biogases to be transported for use in the fuel production process. In one embodiment, less than 5% of the $CO_2$ is removed during the partial purification.

In this embodiment, the centralized processing facility is a fuel production facility that produces a fuel (e.g., ethanol, butanol, etc.) from the partially purified biogas. More specifically, the centralized processing facility includes a methane reformer and a gas fermenter, the latter of which produces the fuel (e.g., ethanol) from a gas stream containing $H_2$ and $CO_2$, and/or CO using appropriate microorganisms. Syngas fermentation is well known in the art. For example, acetogens, which are obligate anaerobes that use the acetyl CoA pathway, are able to use gases containing $CO_2$ and $H_2$, and/or CO to produce acetic acid and ethanol according to the following stoichiometries:

$$2CO_2 + 4H_2 \rightarrow CH_3COOH + H_2O \qquad (7)$$

$$2CO_2 + 6H_2 \rightarrow C_2H_5COH + 3H_2O \qquad (8)$$

$$4CO + 2H_2O \rightarrow CH_3COOH + 2CO_2 \qquad (9)$$

$$6CO + 3H_2O \rightarrow C_2H_5COH + 4CO_2 \qquad (10)$$

In one embodiment, the microorganism is an anaerobic bacteria from the genus *Clostridium*, which is known to produce ethanol from gas streams containing CO, $CO_2$, and $H_2$. In one embodiment, the microorganism used includes any bacteria from a genus selected from *Acetogenium, Acetobacterium, Acetoanaerobium, Butyribacterium* and *Clostridium*. In one embodiment, the microorganism used to produce ethanol is *Clostridium ljungdahlii*. In one embodiment, the microorganism is an acetogen. In one embodiment, the microorganism produces ethanol, butanol, acetate, or butyrate from a gas stream containing $H_2$ and $CO_2$, or from a gas stream containing CO.

In one embodiment, the gas stream containing $H_2$ and $CO_2$, and/or CO is obtained by feeding the partially purified biogas into the methane reformer (e.g., directly or following further purification and/or pre-reforming). For example, if the methane reformer is a SMR, it may be advantageous to subject partially purified biogas having a relatively high $CO_2$ content to an upstream $CO_2$ removal step. In contrast, if the methane reformer is a DMR, the same partially purified biogas may have a $CH_4:CO_2$ that is close enough to the desired ratio that no further $CO_2$ removal is required.

In general, DMR is often associated with a reduced $H_2$ yield as a result of the reverse water gas shift reaction (R-WGS) in which $H_2$ reacts with $CO_2$ to produce CO and $H_2O$.

$$CO_2 + H_2 \rightarrow CO + H_2O \qquad (11)$$

However, in the process depicted in FIG. 6, DMR may be advantageous because more of the $CO_2$ may be converted to ethanol.

In general, the reforming process and/or conditions will be selected to provide the desired $H_2$:CO ratio and/or $CO:CO_2$ ratios for the selected gas fermentation. In one embodiment, the methane reformer includes a WGS reactor. In one embodiment, the methane reformer does not include a WGS reactor.

In one embodiment, the reforming process and/or conditions are selected to provide $H_2$ in excess of the amount of $CO_2$ in order to satisfy the stoichiometric molar ratio of $H_2:CO_2$ of 3:1 to produce ethanol. In one embodiment, additional $H_2$ and/or $CO_2$ is added to the syngas produced by the reforming process in order to provide the desired stoichiometric ratio. In one embodiment, the feed to the gas fermentation has an $H_2:CO_2$ molar ratio from 2:1 to 4:1 or from 2.5:1 to 3.5 to 1.

In one embodiment, the centralized processing facility includes a $CO_2$ removal system (e.g., a membrane system) that receives the partially purified biogases as they are removed from the respective mobile storage systems. The $CO_2$ removal system provides a $CH_4$ rich stream, which is fed to the methane reformer, and a $CO_2$ rich stream, which in one embodiment is fed to the gas fermentation, and in one embodiment, is fed to a R-WGS to produce CO that is fed to the gas fermentation. Advantageously, these embodiments allow biogenic carbon from both the $CH_4$ and the $CO_2$ in the biogas to be incorporated into the ethanol. In one embodiment, additional $H_2$ (e.g., from fossil sources and/or biogenic sources) is added to allow more $CO_2$ to be converted to ethanol.

In addition to the feed gas, the fermentation reactor may be fed a liquid nutrient broth containing the bacterial components required for their growth (e.g., vitamins and salts). In one embodiment, the fermentation reactor is one of a plurality of reactors. In one embodiment, the fermentation reactor is a stirred or an unmixed tank reactor (e.g., deep tank bioreactor, which is a reactor generally having a depth of greater than 10 meters). In one embodiment, the gases are introduced at the bottom region of the fermentation reactor and bubble through the liquid broth. In one embodiment, the gas fermentation employs cell recycle in order to replenish the concentration of cells. In this embodiment, a liquid stream comprising cells is withdrawn from the reactor and sent to a solids-liquid separation (e.g., a microfiltration system or cell-retention system) to separate cells from the stream. The separated cells are returned to the fermentation reactor and a cell-free stream resulting from the separation may be sent to product recovery (e.g., for ethanol product recovery may include distillation). Product recovery and/or cell recycle may be continuous or intermittent. In one embodiment, gases that accumulate in the headspace of the fermentation reactor are recycled back to the fermentation reactor, or are fed back to the methane reformer (e.g., either as feedstock or as fuel). In one embodiment, the gas fermentation is conducted at a temperature between about 20° C. and about 50° C., between about 25° C. and about 45° C., or between about 30° C. and about 40° C. In one embodiment, the gas fermentation is conducted at a pH between about 3 and 8, between about 4 and 7, or between about 4.5 and 6.5. In one embodiment, the gas fermentation is conducted at a pH below about 5 (e.g., and above about 3).

In one embodiment, the gas fermentation process is integrated with an ethanol production process wherein fermentable carbohydrate (e.g., corn, sugar cane, or sugar derived from cellulosic feedstock) is converted to ethanol in a carbohydrate fermentation (e.g., using yeast). For example, in one embodiment, the $CO_2$ produced during the carbohydrate fermentation may be combined with the syngas produced in the methane reformer and/or $CO_2$ from the biogas in order to improve the yield. Alternatively, or additionally, additional hydrogen is added. In one embodiment, the ethanol produced from the gas fermentation is recovered together with the ethanol from the yeast fermentation, which further reduces costs. For example, in one embodiment, ethanol produced from the gas fermentation is transported to the carbohydrate fermentation facility, and provided to the process such that ethanol from the gas fermentation and the carbohydrate fermentation are recovered together. For example, see U.S. Pat. No. 10,202,622.

Advantageously, this embodiment provides a relatively low cost method of producing ethanol (e.g., cellulosic ethanol).

Further advantageously, this embodiment ferments the syngas in order to produce the fuel (e.g., ethanol). In terms of producing a fuel from syngas, gas fermentation has many advantages over other fuel production processes. For example, it typically requires lower temperature and pressure conditions, typically has a higher reaction specificity, and/or may tolerate higher amounts of sulfur compounds. However, one challenge regarding the production of ethanol from syngas fermentation is the feedstock.

While reformed natural gas, waste streams from steel manufacturing, or gasified coal, cokes, and/or oil shale may be used as a feedstock for syngas fermentation, the resulting ethanol is not renewable. In contrast, syngas produced by the gasification of biomass (e.g., municipal organic wastes, switchgrass, etc.) can be fermented to provide a biogenic ethanol. However, since the biomass may need to go through a pretreatment (e.g., drying, size reduction, pyrolysis, leaching, etc.) prior to gasification, there can be significant capital expense, in addition to the cost of feedstock. Moreover, there may be some variation in the $H_2$ content and/or the potential for undesirable compounds.

The processes described herein, where biogas is partially purified at a plurality of respective pre-processing sites before being transported to a centralized processing facility, offers various improvements and/or advantages over other processes of producing a fuel from biogenic syngas. For example, since the syngas is produced from partially purified biogas the feed composition may be substantially constant and/or may contain some $CO_2$. In addition, it facilitates using biogas from relatively small scale biogas producers for fuel production.

In general, the minimum economic scale for a gas fermentation plant and/or a fuel production facility is larger than a typical biogas source can provide. While the input/outputs may be increased by importing RNG from a natural gas distribution system, the cost is relatively high. Alternatively, it has been proposed to collect biogas using a dedicated biogas pipeline. Unfortunately, building a dedicated pipeline may not be economically and/or physically feasible for all biogas producers. However, by transporting or arranging for the transport of partially purified biogases from a plurality of respective sources, the cost of transport is reduced and/or the cost of fully upgrading the biogas to RNG (before transport) is avoided. These cost reductions can be used to offset the cost of transporting the partially purified biogas by vehicle.

Figure 7:
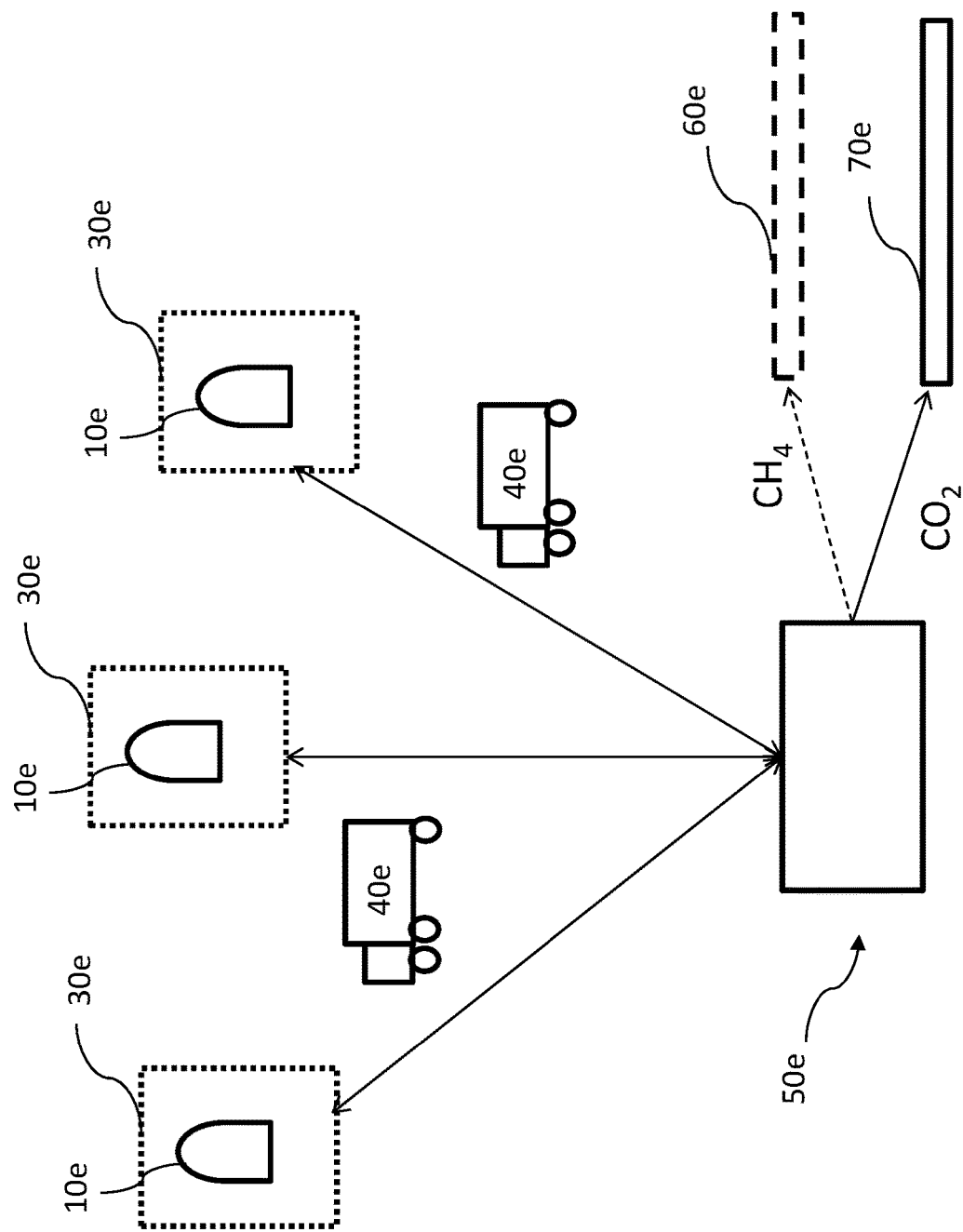
FIG. 7 is a schematic diagram showing a system for providing a fuel in accordance with one embodiment.

FIG. 7 shows a system in accordance with another embodiment. The system includes a plurality of pre-processing sites 30e, each of which includes a source of biogas 10e (e.g., feed from landfill or anaerobic digester), and optionally includes a) a partial purification system (i.e., for removing $H_2O$, $H_2S$, and/or $CO_2$ from the raw biogas), b) a compressor system, and/or c) one or more mobile storage systems (not shown). The system also includes a collection system 40e that includes one or more vehicles (e.g., trucks, ships, or rail cars) for transporting biogas provided at each pre-processing site to the centralized processing facility 50e (e.g., direct route, in a vessel).

Advantageously, since the centralized processing facility 50e can receive biogas (i.e., raw or partially purified) from a plurality of pre-processing sites, it can be a relatively large-scale facility and may profit from the economies of scale. However, one disadvantage of this system is that any biofuel produced from the biogas (e.g., RNG, ethanol, methanol, etc.) can have an adverse carbon intensity impact that can reduce the value of the fuel (e.g., from a sustainability perspective). For example, the carbon intensity of the fuel produced using the system in FIG. 7 can be adversely impacted as a result of energy required for compression of the biogas at the pre-processing sites, particularly when the biogas has a relatively large $CO_2$ content, and/or as a result of transporting the biogas by vehicle, both of which have associated GHG emissions. The term "carbon intensity" or "CI" refers to the quantity of lifecycle GHG emissions, per unit of fuel energy, and is often expressed in grams of carbon dioxide equivalent emissions per unit of fuel (e.g., gCO2e/MJ or gCO2e/MMBTU). In general, the CI and/or lifecycle GHG emissions of a fuels may be calculated using any suitable method (e.g., any method recognized by the applicable regulatory authority). The CI values recited herein are determined using the CA-GREET model (e.g., see, ww2.arb.ca.gov/resources/documents/lcfs-life-cycle-analysis-models-and-documentation), unless otherwise specified.

In the system illustrated in FIG. 7, the centralized processing facility 50e also includes or is connected to a system 70e configured for distributing $CO_2$ collected at the centralized processing facility (e.g., removed from the biogas in the biogas upgrading and/or collected from the methane reforming of biogas). In some embodiments, the centralized processing facility 50e also includes or is connected to a system 60e for distributing any upgraded biogas (e.g., RNG) produced by the biogas upgrading system. In one embodiment, the optional system 60e includes an injection system for injecting the upgraded biogas into a natural gas distribution system. In one embodiment, the optional system 60e for distributing the upgraded biogas includes a truck for transporting pressurized gas. In one embodiment, the system 70e for distributing the $CO_2$ removed from the biogas includes a compressor for compressing the $CO_2$ prior to injection into a $CO_2$ pipeline. In one embodiment, the system 70e for distributing the $CO_2$ includes a truck for transporting the $CO_2$ (e.g., as a liquid).

The $CO_2$ distribution system 70e makes the $CO_2$ available for sequestration, where it is used and/or stored so as to prevent its release into the atmosphere. For example, sequestering $CO_2$ can include using the $CO_2$ for the production of chemicals and/or products, permanently storing the $CO_2$ underground in geological formations (e.g., deep saline formations or abandoned oil and/or gas fields), or using the $CO_2$ for enhanced oil recovery (EOR). Sequestering $CO_2$ derived from the biogas (e.g., $CO_2$ removed during biogas upgrading and/or $CO_2$ produced by reforming the upgraded biogas) is advantageous as it can reduce the lifecycle GHG emissions and/or CI of the fuel produced using the biogas. More specifically, as $CO_2$ derived from the biogas is biogenic, and removing the biogenic $CO_2$ from the atmosphere (or preventing its release to the atmosphere) provides the foundation for carbon removal or negative emissions, the CI of the fuel can be reduced. The term "biogenic carbon dioxide", as used herein, refers to carbon dioxide from biological sources (i.e., not fossil sources).

While reducing greenhouse gas emissions, and in particular providing negative emissions, is advantageous, there is generally a cost and/or feedstock availability barrier to the widespread use of carbon capture and sequestration with biogenic $CO_2$ from biogas. Some of the systems and/or methods described herein provide a number of advantages that improve the economic viability of carbon capture and sequestration with biogenic $CO_2$ from biogas, and can be used to reduce the CI of the fuel produced.

One barrier to the widespread use of carbon capture and sequestration with biogenic $CO_2$ from biogas is supply (e.g., including relatively small-scale sources). In many of the systems and method described herein, the centralized processing facility receives biogas from a plurality of biogas sources, which can be upgraded to provide a substantially continuous supply of biogenic $CO_2$. This is particularly advantageous in embodiments where the pre-processing sites provide no or minimal $CO_2$ removal. In one embodiment, each pre-processing site provides a partial purification that removes less than 5% of the $CO_2$, less than 10% of the $CO_2$, less than 15% of the $CO_2$, less than 20% of the $CO_2$, less than 25% of the $CO_2$, less than 30% of the $CO_2$, less than 35% of the $CO_2$, less than 40% of the $CO_2$, less than 50% of the $CO_2$, less than 60% of the $CO_2$, less than 70% of the $CO_2$, or less than 75% of the $CO_2$, from the raw biogas. Advantageously, the aggregation of $CO_2$ and biogas from a plurality of sources to a centralized biogas processing facility with $CO_2$ sequestration overcomes the economic barrier of sequestering $CO_2$ from individual small scale biogas sources.

While retaining a substantial portion of the $CO_2$ in the biogas for transport advantageously provides more $CO_2$ for sequestration, the presence of relatively large amounts of $CO_2$ for transport increases the cost and GHG emissions (e.g., due to the compression of the relatively impure biogas). In one embodiment, sufficient $CO_2$ is captured and sequestered to offset the GHG emissions attributed to compressing and transporting the raw biogas or partially purified biogas. In one embodiment, a sufficient amount of $CO_2$ is captured and sequestered to reduce a carbon intensity of the fuel produced by at least 5 gCO2e/MJ, at least 10 gCO2e/MJ, at least 15 gCO2e/MJ, at least 20 gCO2e/MJ, at least 25 gCO2e/MJ, at least 30 gCO2e/MJ, at least 35 gCO2e/MJ, or at least 40 gCO2e/MJ, relative to no sequestration of the $CO_2$.

Another barrier to the widespread use of carbon capture and sequestration with biogenic $CO_2$ from biogas is cost. For example, some of the high costs can be related to (i) the limited supply of biogenic $CO_2$, (ii) the capture of the biogenic $CO_2$, and/or (iii) transporting the biogenic $CO_2$ for sequestration. Many embodiments described herein address the first two points by providing centralized biogas upgrading, which can provide a substantially continuous supply of $CO_2$, and which can inherently include carbon capture. The third point, the transport of the $CO_2$ for sequestration, can be a significant source of the high costs. In order to transport $CO_2$ for sequestration, the $CO_2$ typically requires significant compression and/or cooling. When $CO_2$ is transported by vehicle (e.g., truck, ship) it is often transported as a liquid (e.g., a pressure of about 290 psig and a temperature of about −20° C., or a pressure of about 100 psig and a temperature of about −50° C.). When $CO_2$ is transported by pipeline it is often transported as a supercritical fluid (critical point is ~31° C., ~1070 psig). For example, many $CO_2$ pipelines are operated between about 1250 psig and about 2200 psig, or higher. In some embodiments, the collected $CO_2$ is also stored locally at a relatively high pressure (e.g., ~1600 psig) prior to transport by pipeline. In general, the $CO_2$ can be compressed to the desired pressure using a gas compressor, or alternatively, the collected $CO_2$ can be liquified at a lower pressure using a refrigeration system (e.g., 235 psig) and then pumped to the desired pressure. In each case, processing the $CO_2$ for transport can be associated with relatively high compression costs.

In some of the systems and method described herein, the cost of transporting the $CO_2$ and/or the GHG emissions associated with the same, are reduced by using the relatively high pressure of the transported biogas to reduce downstream compression costs. For example, in some embodiments, the biogas transported to the centralized processing facility is provided directly to the biogas upgrading unit at a relatively high pressure (e.g., at least 25 psig, at least 50 psig, at least 75 psig, at least 100 psig, at least 150 psig, at least 200 psig, at least 250 psig, at least 300 psig, at least 400 psig, at least 500 psig, or at least 600 psig) without passing through a compressor (e.g., is passed through a pressure let down system configured to provide the desired feed pressure for the biogas upgrading). As many $CO_2$ removal units configured to operate at relatively high feed pressures can be also configured to directly provide a $CO_2$ stream at a relatively high pressure (e.g., at least 25 psig, at least 50 psig, at least 75 psig, at least 100 psig, at least 150 psig, at least 200 psig, at least 250 psig, at least 300 psig, or at least 400 psig), this can further reduce the compressions costs and/or cooling costs associated with compression. The savings related to reduced compression requirements can be significant as the cost of compression can be dependent on the starting pressure. The energy consumed in compressing is related to the percent change in absolute pressure. When a low pressure gas undergoes a compression, the increase in the absolute pressure measurement (e.g., psia) is smaller than a higher pressure gas undergoing the same degree of compression. By way of example, the energy required to compress a quantity of gas (e.g., mass or standard volume) from atmospheric pressure to 50 psig (i.e., 15 psia to 65 psia, or 4.3x) can be used to compress the same quantity of gas at 65 psia to about 281 psi, or the same quantity of gas at 281 psia to about 1218 psia.

In one embodiment, the biogas upgrading unit includes a $CO_2$ removal unit that provides a $CO_2$ stream at a pressure of at least 25 psig, at least 50 psig, at least 75 psig, at least 100 psig, at least 150 psig, at least 200 psig, at least 250 psig, at least 300 psig, or at least 400 psig, without having to pass the stream of $CO_2$ through a gas compressor.

In general, providing a biogas upgrading system and/or fuel processing facility configured to provide a compressed stream of relatively pure $CO_2$ (e.g., at least 80%, preferably at least 90%, and more preferably at least 95% $CO_2$) improves the efficiency of the process. In some embodiments, the compressed stream of $CO_2$ is provided without passing through a gas compressor (e.g., is compressed as a result of the feed pressure to biogas upgrading). In some embodiments, the stream of $CO_2$ is compressed by a gas compressor downstream of the biogas upgrading. The term "compressed", as used herein with respect to a gas, refers to the gas being contained under pressure. The term "compressed stream of carbon dioxide", as used herein, refers to a stream that is predominantly $CO_2$ and is under pressure. In one embodiment, the compressed stream of carbon dioxide is at least 80% $CO_2$, at least 85% $CO_2$, at least 90% $CO_2$, or at least 95% $CO_2$. Providing a compressed stream of biogenic $CO_2$ from biogas upgrading is relatively uncommon. When upgrading biogas, the separated $CO_2$ is usually released to the atmosphere. For example, when the off-gas from the biogas upgrading contains methane (e.g., methane slip), the off-gas is often combusted to destroy the methane (e.g., flared), and the biogenic $CO_2$ also in the off-gas is released to the atmosphere. This is generally considered acceptable as releasing the biogenic $CO_2$ simply returns to the atmosphere carbon that was previously removed therefrom by plant photosynthesis (e.g., no net change in GHG emissions).

The system illustrated in FIG. 7 can be used in accordance with a number of embodiments of producing a fuel or producing a fuel and/or a $CO_2$ product. In one embodiment, the centralized processing facility 50e includes a biogas upgrading system and the fuel is RNG that is injected into the NG distribution system 60e. In another embodiment, the centralized processing facility 50e includes a biogas upgrading system, which produces RNG for injection into the NG distribution system 60e, and the fuel is produced from NG withdrawn from the NG distribution system 60e and associated with the environmental attributes of the RNG. In yet another embodiment, the centralized processing facility 50e includes a biogas upgrading system and a methane reformer for reforming upgraded biogas as part of a fuel production process to produce the fuel. In these embodiments, the $CO_2$ is collected from raw and/or partially purified biogas, is compressed and/or cooled, is transported, and sequestered (e.g., to reduce the CI of the fuel). For example, in one embodiment, the collected $CO_2$ is compressed and/or cooled to provide supercritical $CO_2$. In one embodiment, the supercritical $CO_2$ is for transported by pipeline for sequestration underground in one or more geological formations such as a deep saline formation or for use in EOR. In one embodiment, the collected $CO_2$ is cooled to provide solid or liquid $CO_2$ for transport by vehicle.

In accordance with one embodiment (#1) there is provided a method for producing a fuel from biogas comprising: (a) providing biogas from a plurality of biogas sources, the biogas from each biogas source produced in a process comprising: (i) collecting raw biogas from one of the biogas sources in the plurality, the raw biogas comprising methane and $CO_2$; (ii) optionally, subjecting the raw biogas to a partial purification to produce partially purified biogas, wherein the partial purification removes water and removes less than 75% of the $CO_2$ from the raw biogas;(iii) filling a vessel with the raw biogas or the partially purified biogas to a pressure of at least 1500 psig; (iv) transporting the filled vessel to a centralized processing facility by vehicle; and (v) removing the raw biogas or the partially purified biogas from the vessel transported to the centralized processing facility; (b) producing a fuel in a fuel production process, the fuel production processing comprising feeding the biogas provided in step (a) to a biogas upgrading system, the biogas upgrading system configured to remove $CO_2$ from the biogas; (c) processing the $CO_2$ removed in (b) for transport by vehicle, pipeline, or a combination thereof, the processing comprising cooling, compressing, or a combination thereof; and (d) sequestering the $CO_2$ processed in (c), thereby reducing a carbon intensity of the fuel produced in the fuel production process, the sequestering comprising sequestering an amount of $CO_2$ sufficient to substantially offset greenhouse gas emissions attributed to compressing and transporting the raw biogas or partially purified biogas. In one embodiment (#2), step (ii) comprises subjecting the raw biogas to a partial purification to produce partially purified biogas. In one embodiment (#3), the method in any of embodiments #1 to #2 comprises sequestering a sufficient amount of $CO_2$ provided in step (c) to reduce a carbon intensity of the fuel produced in (b) by at least 10 gCO2e/MJ relative to no sequestration of the $CO_2$. In one embodiment (#4), step (c) in any of embodiments #1 to #3 comprises providing the $CO_2$ as a liquid or a supercritical fluid. In one embodiment (#5), in the method in any of embodiments #1 to #4, the biogas upgrading system is configured to provide the stream of $CO_2$ at a pressure of at least 50 psig without passing the stream of $CO_2$ through a gas compressor. In one embodiment (#6), the method in any of embodiments #1 to #5 comprises passing biogas removed in step (v) through a pressure let down system that provides the removed biogas at a pressure of at least 200 psig, and wherein step (b) comprises feeding the biogas at the pressure of at least 200 psig into the biogas upgrading system. In one embodiment (#7), in the method in any of embodiments #1 to #6, the partial purification does not include $CO_2$ removal. In one embodiment (#8), in the method in any of embodiments #1 to #6, the partial purification consists of water removal. In one embodiment (#9), in the method in any of embodiments #1 to #8, the fuel production process comprises reforming upgraded biogas, and wherein the method comprises sequestering $CO_2$ produced by the reforming. In one embodiment (#10), in the method in any of embodiments #1 to #9, the fuel is renewable natural gas. In one embodiment (#11), in the method in any of embodiments #1 to #9, the fuel is renewable hydrogen, renewable methanol, renewable ethanol, gasoline having renewable content, diesel having renewable content, or dimethyl ether. In one embodiment (#12), in the method in any of embodiments #1 to #11, the biogas upgrading system includes a $CO_2$ removal unit that provides organic physical scrubbing, chemical scrubbing, pressure swing adsorption, membrane separation, or cryogenic upgrading. In one embodiment (#13), step (iii) of the method in any of embodiments #1 to #12, comprises filling the vessel with the raw biogas to a pressure of at least 1500 psig. In one embodiment (#14), in the method in any of embodiments #1 to #13, step (ii) comprises subjecting the raw biogas to a partial purification to produce partially purified biogas, wherein the partial purification removes less than 50% of the $CO_2$ from the raw biogas. In one embodiment (#15), in the method in any of embodiments #1 to #14, step (iii) comprises transporting the filled vessel directly to a centralized processing facility by vehicle.

Of course, the above embodiments have been provided as examples only. It will be appreciated by those of ordinary skill in the art that various modifications, alternate configurations, and/or equivalents will be employed without departing from the spirit and scope of the invention. Accordingly, the scope of the invention is therefore intended to be limited solely by the scope of the appended claims.

The invention claimed is:

1. A method for producing fuel from biogas comprising:
   (a) providing biogas from a plurality of biogas sources, the biogas from each biogas source produced in a process comprising:
   (i) collecting raw biogas from one of the biogas sources in the plurality, the raw biogas comprising methane and carbon dioxide;
   (ii) optionally, subjecting the raw biogas to a partial purification to produce partially purified biogas, wherein the partial purification removes less than 75% of the carbon dioxide from the raw biogas;
   (iii) filling a vessel with the raw biogas or the partially purified biogas to a pressure of at least 1500 psig;
   (iv) transporting the filled vessel to a centralized processing facility by vehicle; and
   (v) removing the raw biogas or the partially purified biogas from the vessel transported to the centralized processing facility;
   (b) producing fuel in a fuel production process, the fuel production processing comprising feeding the biogas provided in step (a) to a biogas upgrading system, the biogas upgrading system configured to provide a compressed stream of carbon dioxide removed from the biogas; and
   (c) providing carbon dioxide from the compressed stream of carbon dioxide for transport by vehicle, pipeline, or a combination thereof.

2. The method according to claim 1, wherein step (iv) comprises transporting the filled vessel directly to the centralized processing facility by vehicle.

3. The method according to claim 2, wherein step (ii) comprises subjecting the raw biogas to a partial purification to produce partially purified biogas.

4. The method according to claim 3, comprising sequestering a sufficient amount of carbon dioxide provided in step (c) to reduce a carbon intensity of the fuel produced in (b) by an amount that substantially offsets greenhouse gas emissions attributed to compressing and transporting the raw biogas or partially purified biogas.

5. The method according to claim 3, comprising sequestering a sufficient amount of carbon dioxide provided in step (c) to reduce a carbon intensity of the fuel produced in (b) by at least 10 gCO2e/MJ relative to no sequestration of the carbon dioxide.

6. The method according to claim 3, wherein step (c) comprises providing the carbon dioxide as a liquid or a supercritical fluid.

7. The method according to claim 3, wherein the biogas upgrading system is configured to provide the compressed stream of carbon dioxide at a pressure of at least 50 psig without passing the compressed stream of carbon dioxide through a gas compressor.

8. The method according to claim 1, comprising sequestering a sufficient amount of carbon dioxide provided in step (c) to reduce a carbon intensity of the fuel produced in (b) by an amount that offsets greenhouse gas emissions attributed to compressing and transporting the raw biogas or partially purified biogas.

9. The method according to claim 1, comprising sequestering a sufficient amount of carbon dioxide provided in step (c) to reduce a carbon intensity of the fuel produced in (b) by at least 10 gCO2e/MJ relative to no sequestration of the carbon dioxide.

10. The method according to claim 1, wherein step (c) comprises providing the carbon dioxide as a liquid or a supercritical fluid.

11. The method according to claim 1, wherein the biogas upgrading system is configured to provide the compressed stream of carbon dioxide at a pressure of at least 50 psig without passing the compressed stream of carbon dioxide through a gas compressor.

12. The method according to claim 11, comprising passing biogas removed in step (v) through a pressure let down system that provides the removed biogas at a pressure of at least 200 psig, and wherein step (b) comprises feeding the biogas at the pressure of at least 200 psig into the biogas upgrading system.

13. The method according to claim 1, comprising passing biogas removed in step (v) through a pressure let down system that provides the removed biogas at a pressure of at least 200 psig, and wherein step (b) comprises feeding the biogas at the pressure of at least 200 psig into the biogas upgrading system.

14. The method according to claim 1, wherein step (ii) comprises subjecting the raw biogas to a partial purification to produce partially purified biogas, and wherein the partial purification does not include carbon dioxide removal.

15. The method according to claim 1, wherein step (ii) comprises subjecting the raw biogas to a partial purification to produce partially purified biogas, and wherein the partial purification consists of water removal.

16. The method according to claim 1, wherein the fuel production process comprises reforming upgraded biogas, and wherein the method comprises sequestering carbon dioxide produced by the reforming.

17. The method according to claim 1, wherein the fuel is renewable natural gas.

18. The method according to claim 1, wherein the fuel is renewable hydrogen, renewable methanol, renewable ethanol, gasoline having renewable content, diesel having renewable content, or dimethyl ether.

19. The method according to claim 1, wherein the biogas upgrading system includes a carbon dioxide removal unit that provides organic physical scrubbing, chemical scrubbing, pressure swing adsorption, membrane separation, or cryogenic upgrading.

20. The method according to claim 1, wherein step (iii) comprises filling the vessel with the raw biogas to a pressure of at least 1500 psig.

21. The method according to claim 1, wherein step (ii) comprises subjecting the raw biogas to a partial purification to produce partially purified biogas, and wherein the partial purification removes less than 50% of the carbon dioxide from the raw biogas.

* * * * *